(12) United States Patent
Copland et al.

(10) Patent No.: US 12,285,214 B2
(45) Date of Patent: Apr. 29, 2025

(54) WIDE-FIELD MULTI-AXIS ABERROMETER

(71) Applicant: Wavefront Dynamics, Inc., Albuquerque, NM (US)

(72) Inventors: James Copland, Albuquerque, NM (US); Daniel R. Neal, Tijeras, NM (US); Lyle Kordonowy, Sandia Park, NM (US)

(73) Assignee: Wavefront Dynamics Inc., Albuquerque, NM (US)

( * ) Notice: Subject to any disclaimer, the term of this patent is extended or adjusted under 35 U.S.C. 154(b) by 249 days.

(21) Appl. No.: 17/180,838

(22) Filed: Feb. 21, 2021

(65) Prior Publication Data

US 2021/0263338 A1 Aug. 26, 2021

Related U.S. Application Data

(60) Provisional application No. 62/980,097, filed on Feb. 21, 2020, provisional application No. 62/980,337, filed on Feb. 23, 2020.

(51) Int. Cl.
| | |
|---|---|
| *A61B 3/10* | (2006.01) |
| *A61B 3/00* | (2006.01) |
| *A61B 3/103* | (2006.01) |
| *A61B 3/107* | (2006.01) |
| *A61B 3/14* | (2006.01) |
| *G01B 11/24* | (2006.01) |
| *G01M 11/02* | (2006.01) |
| *G02C 7/02* | (2006.01) |
| *G02C 7/04* | (2006.01) |

(Continued)

(52) U.S. Cl.
CPC .......... *A61B 3/1015* (2013.01); *A61B 3/0091* (2013.01); *A61B 3/102* (2013.01); *A61B 3/103* (2013.01); *A61B 3/107* (2013.01); *A61B 3/14* (2013.01); *G01B 11/24* (2013.01); *G01M 11/0242* (2013.01); *G02C 7/027* (2013.01); *G02C 7/04* (2013.01); *G02C 7/047* (2013.01); *G02C 7/049* (2013.01); *G05B 19/4099* (2013.01); *G06T 7/521* (2017.01); *G06T 7/55* (2017.01); *G16H 50/30* (2018.01); *G16H 50/70* (2018.01); *B33Y 50/00* (2014.12); *B33Y 80/00* (2014.12); *G02C 2202/24* (2013.01); *G05B 2219/35134* (2013.01); *G05B 2219/36199* (2013.01); *G05B 2219/36204* (2013.01); *G05B 2219/49023* (2013.01); *G06T 2207/10028* (2013.01); *G06T 2207/30041* (2013.01)

(58) Field of Classification Search
CPC .............................. A61B 3/1015; A61B 3/102
USPC .................................................. 351/205, 247
See application file for complete search history.

(56) References Cited

U.S. PATENT DOCUMENTS

| | | | |
|---|---|---|---|
| 5,208,619 A | 5/1993 | Campbell | |
| 6,550,917 B1 * | 4/2003 | Neal | G02C 7/027 351/221 |

(Continued)

*Primary Examiner* — Zachary W Wilkes
(74) *Attorney, Agent, or Firm* — Quinn IP Law

(57) ABSTRACT

This invention relates to optical methods and optical systems for making both on-axis and wide-field, peripheral off-axis wavefront measurements of an eye; and for designing and manufacturing wavefront-guided customized contact lens useful for myopia control. The wide-field optical instrument can comprise either (1) a multi-axis optical configuration using multiple off-axis beamlets, or (2) an instrument comprising a rotatable scanning mirror that generates off-axis probe beams.

8 Claims, 24 Drawing Sheets

(51) Int. Cl.
    *G05B 19/4099*     (2006.01)
    *G06T 7/521*     (2017.01)
    *G06T 7/55*     (2017.01)
    *G16H 50/30*     (2018.01)
    *G16H 50/70*     (2018.01)
    *B33Y 50/00*     (2015.01)
    *B33Y 80/00*     (2015.01)

(56) References Cited

U.S. PATENT DOCUMENTS

| | | | |
|---|---|---|---|
| 6,634,750 B2 | 10/2003 | Neal | |
| 7,339,658 B2 * | 3/2008 | Beyerlein | A61B 3/107 |
| | | | 356/73 |
| 7,488,070 B2 * | 2/2009 | Hauger | G01J 9/00 |
| | | | 351/200 |
| 7,762,667 B2 | 7/2010 | Adino | |
| 7,909,465 B2 * | 3/2011 | Ho | A61B 3/103 |
| | | | 351/221 |
| 7,976,163 B2 | 7/2011 | Campbell | |
| 8,260,024 B2 | 9/2012 | Farrer | |
| 9,022,570 B2 | 5/2015 | Applegate | |
| 9,445,717 B2 * | 9/2016 | Ehrmann | A61B 3/0008 |
| 9,486,137 B2 | 11/2016 | Raymond | |
| 9,504,576 B2 | 11/2016 | Neal | |
| 9,554,889 B2 | 1/2017 | Johns | |
| 9,658,470 B2 | 5/2017 | Applegate | |
| 9,737,204 B2 * | 8/2017 | Wall | A61B 3/12 |
| 10,485,417 B2 | 11/2019 | Copland | |
| 10,506,923 B2 | 12/2019 | Neal | |
| 10,555,669 B2 | 2/2020 | Pulaski | |
| 10,682,056 B2 | 6/2020 | Neal | |
| 2003/0038921 A1 * | 2/2003 | Neal | A61B 3/1015 |
| | | | 351/212 |
| 2006/0209256 A1 * | 9/2006 | Beyerlein | A61B 3/103 |
| | | | 351/212 |
| 2013/0128224 A1 * | 5/2013 | Wall | A61B 3/0008 |
| | | | 351/221 |
| 2014/0139804 A1 * | 5/2014 | Ehrmann | A61B 3/0008 |
| | | | 351/205 |

\* cited by examiner

With contacts (+1.5D peripheral add)

WIDE-FIELD MULTI-AXIS ABERROMETER

CROSS-REFERENCES TO RELATED APPLICATIONS

This application claims a priority benefit of U.S. Provisional 62/980,097 filed Feb. 21, 2020; and U.S. Provisional 62/980,337 filed Feb. 23, 2020, both of which are incorporated herein by reference in their entirety.

FIELD OF THE INVENTION

The general field of the invention includes ophthalmology and optometry, and the use of optical instruments (aberrometers) that use wavefront sensors for measuring on-axis (central vision) and wide-field, off-axis (peripheral vision) aberrations of an eye's optical properties. Customized contact lenses can be made that correct for these measured aberrations, which can be used for controlling the progression of myopia over time.

BACKGROUND OF THE INVENTION

Doctors lack a general methodology for writing prescriptions of myopia control contact lenses (CL) for effective treatment. About the age of twelve, many people start to develop myopia, typically at a rate of one diopter per year, until myopia progression stops on its own at about age twenty.

Many people end up strongly myopic, which is associated with eye health risks such as retinal detachments and vision that cannot be corrected to better than about 20/30 by any means. Doctors can prescribe "myopia control contact lenses" that slow the rate of progression to about half a diopter a year. But that only works in about half of the patients. Doctors have no means of telling if a specific contact lens will work or if a different lens would be better.

The common situation is that doctors prescribe myopia control contact lenses, send the patient away, then have them come back six months later and see if the rate of myopia progression has slowed. Such an exam may simply employ using a phoropter, or it may also include use of an OCT system to measure axial eye length. Increased axial eye length is the direct physical parameter that relates to increased myopia.

Some people have proposed measuring the contact lens on the eye on-axis and looking at the spherical aberration value. Even this simple idea has not become common. It may have some correlation to the off-axis refraction. But it is not the same thing as measuring the proper off-axis refraction that is believed to be cause of myopia progression.

Some researchers have been measuring off-axis refractions of the bare eye and with contact lenses. But the measurements are done with instruments that are single axis. A graph of refraction versus gaze angle is created with sequential measurements, with the patient re-directing their gaze in-between measurements. The problem is that young people's eyes will change in focus between measurements. So, to get meaningful results the doctors apply cycloplegic eye drops so the eye is fixed at far focus. This provides repeatable measurements.

However, it does not re-create the conditions the eye experiences with normal activities, which results in myopia progression. It is believed that some abnormality in how the eye is focused is causing the myopia progression, particularly since increased incidence of myopia progression is associated with prolonged near work. Also lack of outdoor activity which involve far focus tasks has been correlated with increasing myopia progression.

One theory for the cause of myopia progression is that as the eye develops from childhood through early adult years it is slowly growing in size and length [Wolffsohn J S, Flitcroft D I, Gifford K L, et al. IMI—Myopia control reports overview and introduction. Invest Ophthalmol Vis Sci. 2019; 60: M1-M19. https://doi.org/10.1167/iovs.18-25980]. It has been proposed that the presence of hyperopic defocus stimulates the eye to continue to grow in length [Sankaridurg P, Bakaraju R C, Naduvilath T, Chen X, Weng R, Tilia D, Xu P, Li W, Conrad F, Smith E L 3rd, Ehrmann K. Myopia control with novel central and peripheral plus contact lenses and extended depth of focus contact lenses: 2 year results from a randomized clinical trial [Ophthalmic Physiol Opt. 2019 July; 39 (4): 294-307. doi: 10.1111/opo.12621. Epub 2019 Jun. 10. PMID: 31180155; PMCID: PMC6851825.]. There are a number of animal and human studies that seem to validate this idea.

Optically, this is because the visual acuity, and hence vision correction, is measured for only the central region, and the periphery is ignored. Once a set of spectacles is prescribed, this corrects the vision on the macula, but causes the periphery to have a hyperopic defocus due to mismatch between the image shell from the spectacles and eye and the shape of the retina. The peripheral defocus, which is a much larger total area, stimulates growth in eye length.

It is also known that peripheral eye growth happens in local regions on the retina in response to local defocus. This is known from experiments with baby chickens. Chicks are useful because they grow rapidly which is convenient for experimentation. Little eyeglasses have been fit to chicks so that half the retina experiences good focus and the other half experiences defocus. Dissection reveals that the area of the retina experiencing defocus grows in eye length while the section experience focus remains with the same eye length. This reveals that the shape of the focus surface in relation to the retinal surface is the key item driving myopia progression. So, by measuring the off-axis refractive profile, we are able to derive information that will directly lead to better design and clinical application of myopia progression contact lenses.

One method that has also been tried is to prescribe conventional eyeglasses or contact lenses that leave some part of the myopia uncorrected. This has been found to be an ineffective treatment. Based on the results with the baby chicks, we would expect that because all that can be achieved with a misadjusted eye glass prescription is an offset from an average desired focus condition, when what is really needed is a particular profile of defocus across the retina.

One method for correcting for peripheral defocus is to use a non-spherical correction in a contact lens. With the addition to some additional power in the periphery of a contact lens, off-axis rays have a higher power, and hence reduce the mismatch between image shell and retinal shape. However, heretofore it has been difficult to measure this off-axis refraction without considerable difficulty and expense (See prior art device in FIGS. 1A and 1B).

There are several different contact lens products that attempt to provide some peripheral defocus for this and other purposes [e.g., MiSight lenses from CooperVision]. In fact, a peripheral Add has long been used to reduce the effects of presbyopia in the aging eye. With these technologies available, a clinician when presented with an emergent case of myopia has many options to try. The question that immediately is presented when dealing with such a case, is "How much Add-power should we use in the periphery?"

FIG. 15A shows a snapshot of a computer screen showing (1) a visual image of the patient's pupil, (2) a contour plot of wavefront measurements, and (3) a table listing the Zernike coefficients for the first twenty-seven Zernike polynomials, for a patient's bare eye, according to the present invention. FIG. 15A is an example of a young subject, age 11, that has presented with a modest amount of myopia. Note that there is a considerable amount of spherical aberration (defocus) present ($Z_2^0$ coefficient), and the RMS value=4.9 microns.

FIG. 15B shows a snapshot of a computer screen showing (1) a visual image of the patient's pupil, (2) a contour plot of wavefront measurements, and (3) a table listing the Zernike coefficients for the first twenty-seven Zernike polynomials, for a patient's bare eye fitted with an initial contact lens (+1.5D Add), according to the present invention. Initially, the lowest ADD value was used (+1.5D). Measuring through these contact lenses, the results shown in FIG. 15B show that the spherical aberration is reduced to nearly zero. However, in order for Smith's peripheral defocus theory to work, it would be necessary to reverse the sign of the subject's spherical aberration.

This brings up a key weakness in this conventional method of myopia control. If the initial state of the subject's ocular aberrations is unknown, it is difficult to achieve the best desired state. In fact, the clinical studies of this method show that only about one-half of the subjects respond to treatment with peripheral-add contacts, and this reduces the progression rate to about one-half [Chalmers R, et al. Ophthalmic Physiol Opt. 2020; doi: 10.1111/opo.12753].

FIG. 16A shows a hypothetical off-axis refraction profile (Sphere, S) that this invention is intended to measure. The horizontal axis is the measurement angle of the measurement off of the line of sight of the eye. The vertical axis is the spherical equivalent refraction of the eye.

FIG. 16B is a hypothetical cylinder off-axis profile (Cylinder, C) that this invention is intended to measure. The horizontal axis is the measurement angle of the measurement off of the line of sight of the eye. The vertical axis is the cylinder refraction of the eye. A similar plot of cylinder axis, A, versus off-axis angle could also be prepared.

Every clinic that prescribes myopia control contact lenses has some patients that respond favorably and other patients that are non-responders, even for the same contact lens design. That likely is because the off-axis performance of a contact lens varies depending on the particular eye it is sitting on.

The goal of this invention is to enable those clinics to measure both responders and non-responders. From that, the doctor can determine which contact-lens-corrected off-axis refractions are effective. Then when future patients are fit with contact lenses, the off-axis refractions are measured. Then the doctor would know immediately if the contact lens chosen would be effective. If the off-axis refractions predicted poor effectiveness, the doctor would know to try a different lens and could potentially titrate the amount of correction to optimize the treatment. This is greatly beneficial to the patient because it eliminates the step of putting a contact lens on a patient and seeing six months later if it slowed myopia progression. Getting a patient into an effective contact lens sooner lessens the degree of myopia that they eventually develop. Thus, a measurement of the patient's initial refractive state would be effective at guiding the course of treatment.

A critical physical characteristic that occurs with myopia progression is eye length growth. As the discussion about baby chickens showed, this can be thought of as overall eye length on the center axis of the eye, but also locally-occurring eye growth across the retina. It is possible to measure the eye length across the retina with a scanning OCT system. This potentially could be useful in understanding myopia progression and an instrument that combines off-axis refraction measurements with scanning OCT could lead to improved understanding and treatment of myopia progression. It should be appreciated however, that a scanning OCT is not able to directly measure the off-axis refractive profile of the eye, and, so, by itself, scanning OCT lacks the ability to measure the critical factor that drives myopia progression. The monitoring of eye length growth over a period of months or years will help determine what off-axis refractive profile provided by the contact lenses are the most effective. It would be convenient to include the OCT system in the present invention, but the present invention used in coordination with a stand-alone OCT system would also be effective.

FIGS. 1A and 1B show a prior art measurement device, named the "EyeMapper" [1], that measures off-axis eye refractions over a range of angles up to +/−40 degrees. It uses a scanning mirror to switch a single wavefront sensor and single probe beam source into multiple (i.e., 11) different objective lenses. This arrangement is different than the present invention (and its alternate embodiments), as described below. The "EyeMapper" is a particularly expensive and complicated instrument.

The data collected with multiple off-axis angles can be used as input for tomographic reconstruction of internal eye structures. A US patent for that concept was issued to Dan Neal and Richard Copland. U.S. Pat. No. 6,634,750B2 "Tomographic wavefront analysis system and method of mapping an optical system".

The second embodiment of an optical device (See FIGS. 5 and 6) in this specification is similar to (but, not the same as) the corneal topographer system described in the patent issued to Dan Neal and Richard Copland, U.S. Pat. No. 6,634,750 "Tomographic Wavefront Analysis System and Method of Mapping an Optical System", which is incorporated herein by reference in its entirety. However, that patent does not mention applying the system to supporting investigations into myopia progression, including making measurements through a contact lens that is fitted on the eye.

BRIEF SUMMARY

This invention relates to optical methods and optical systems for making both on-axis and wide-field, peripheral off-axis wavefront measurements of an eye, and for designing and manufacturing wavefront-guided customized contact lens useful for myopia control.

DETAILED DESCRIPTION OF THE INVENTION

Figure 1A:
FIG. 1A shows a perspective photograph of a prior art device, "EyeMapper" [1].
Figure 1B:
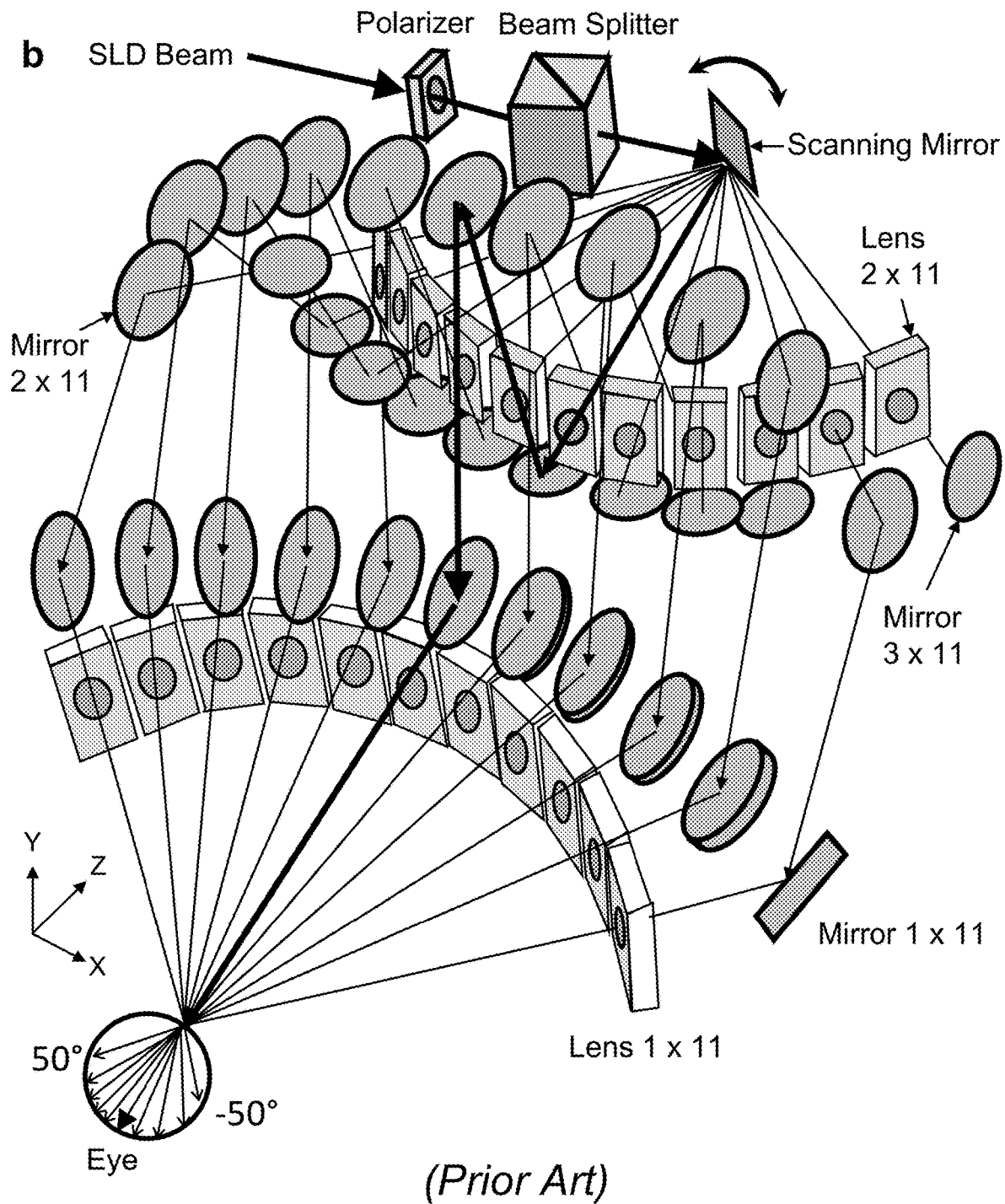
FIG. 1B shows a perspective schematic view of the layout of internal components of a prior art device, "EyeMapper" [1].

The eye is measured with an instrument that delivers a probe beam into the eye at a variety of angles. The arrangement enables both on-axis and off-axis measurements in rapid succession at a speed that is faster than the accommodation of the eye can change, for example within 0.2 seconds. The eye would generally not need to be cyclopleged (i.e., paralyzed) for the measurement, so the eye can be measured in conditions that are the natural conditions which are driving some eyes into myopia progression.

The invention described here is both an instrument and a process of using the instrument to guide prescription of contact lenses for better efficacy in myopia control. Note: the phrase "conventional contact lens" refers to a contact lens that is un-corrected with respect to higher-order aberrations (HOA's) that are measured with a wavefront sensor while looking through the conventional contact lens fitted on the eye (i.e., HOAs are un-corrected when using a conventional contact lens).

The following acronyms are used herein: WF=WaveFront; WFD=WaveFront Dynamics, LLC; WFG=Wavefront Guided; WFE=Wavefront Error; WFS=WaveFront Sensor; LOA=Lower Order Aberration, HOA=Higher Order Aberration, RMS=Root Mean Square; CL=Contact Lens; CCL=Customized Contact Lens; SCA=Sphere, Cylinder, Axis; Pt=patient, SLD=Super Luminescent Diode, Seq=Spherical Equivalent; BS=BeamSplitter; RLA=Range Limiting Aperture; OD=right eye; OS=left eye; DTF=Dynamic Tear Film, HORMS=Higher Order RMS, ECPs=Eye Care Practitioners; MCCL=myopia control contact lens; OCT=Optical Coherence Tomography. All references cited herein are incorporated by reference in their entirety. The words "accommodate" and "accommodative" both refer to the condition where the eye automatically adjusts the shape of its natural crystalline lens to re-focus the eye when the gaze target distance changes. Typically, "accommodation" results in an increase in optical power and a reduction in pupil size. The words "sequential" and "sequence" refers to a dynamic, time-dependent set or series of measurements. increase in optical power (accommodation) and a reduction in pupil size. The phrase "alignment camera" and "Eye Imaging Camera" mean the same thing. The phrase "wide-field" refers to taking measurements at off-axis angles of incidence, so that the peripheral vision is accurately measured by a device that can either use (a) multiple off-axis beamlets, or (b) a scanning mirror that rotates to provide a single off-axis probe beam and many off-axis angles, illuminating the periphery of the eye. The word "aberrometer" is an optical instrument that is broadly construed to include refractometer and autorefractor systems. A "wide-field aberrometer" is an aberrometer that has the capability to measure conventional refraction profiles (including both lower order aberrations (LOAs: Sphere, Cylinder, and Axis), as well as higher order aberrations (HOAs) at off-axis angles of incidence), which allows the periphery of the eye to be accurately measured, as well as measuring the central part of the eye. The HOA's can be described by Zernike polynomials, or a wavefront error surface.

A software package included with the instrument would allow the clinician to associate patients and contact lenses prescriptions and off-axis refraction profiles with clinical observations the doctor has made about if a patient has been effectively treated. Such data could include manifest refractions or measurements of eye axial length the doctor has collected via Optical Coherence Tomography (OCT). The software would analyze the data and generate rules about what contact lenses would be most effective for which eyes. The advantage of such a software package is that it helps the doctor to determine more effective courses of treatment from a retrospective analysis. This is part of the inventive nature of this disclosure.

Figure 22:
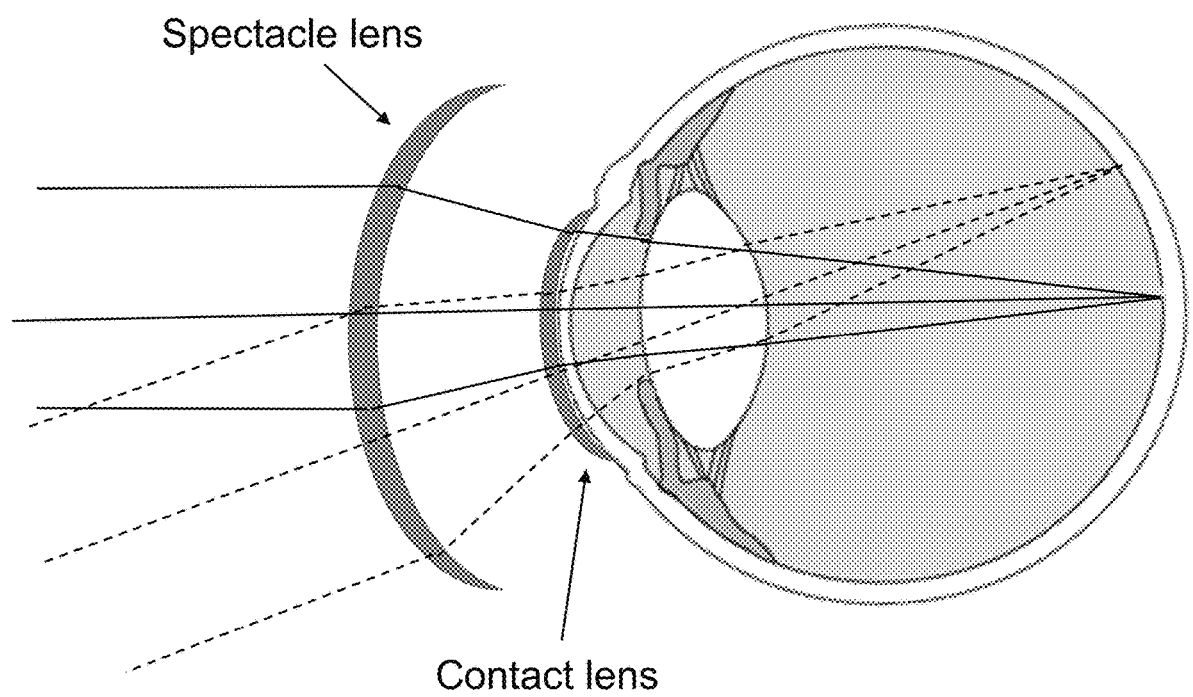
FIG. 22 shows a schematic optical configuration of a tenth embodiment of the present invention.

In order to correct for peripheral defocus, it has been common practice to use a peripheral "add" contact lens. There are now several contact lenses on the market that have been adapted for this purpose. However, optically, a single surface (i.e., the contact lens) is not sufficient to fully specify a lens with good optical quality in the periphery. As is typical in optical design, it would be beneficial to have additional surfaces (additional lens, e.g., doublet lenses). In camera and imaging lenses this is achieved by adding many different optical elements, either in groups, or by cementing them together. This is rather difficult to do with a contact lens. However, another common location for corrective lenses is at the spectacle plane location. It is very common practice to wear glasses for myopia. This would provide another pair of optical surfaces that could be optimized, in conjunction with a special contact lens, to provide better image resolution in both central and peripheral retina. This is rather inconvenient, as the patient would have to wear both contact lenses and glasses, but if myopia could be controlled or even reversed, then it may be worth it for the short term. FIG. 22 shows how multiple optical surfaces can be used to bring both on-axis and peripheral rays into focus. The spectacle plane optics works in conjunction with the contact lens optics and the optics of the eye itself to match the field curvature to the shape of the retina. To design such optics, the shape of the retina (or conversely the off-axis defocus curve) must be measured by using an instrument such as described herein.

Another technique for modifying the refraction that has become common is Orthokeratology. Orthokeratology is the use of a semi-rigid contact lens that is worn prophylactically to change the shape of the cornea to correct vision. The contact lens is worn at night, and the shape and wear pattern are adjusted to improve the subject's vision. One side effect of orthokeratology is that this process also can induce a large amount of spherical aberration [D. R. Neal and F. Chinisci, "Influence of Wavefront Aberration on Visual Performance After Orthokeratology: A Case Study," Investigative Ophthalmology & Visual Science April 2009, Vol. 50, 1573.]. This spherical aberration can serve a similar function to a peripheral "add" contact lens and has been shown to have some efficacy at reducing myopia progression in some patients. In a similar manner to monitoring the progression of spherical aberration when peripheral add contact lenses are used, it would be advantageous to monitor the induction of aberrations caused by orthokeratology. This would require measurement of aberrations of the eye both on-axis and off-axis, as described herein.

A first example of a method of slowing down the progression of myopia in the eye of a patient, using a multi-axis optical instrument, can comprise:

(1) positioning a video fixation target in the instrument at an appropriate location to stimulate a desired accommodation level;
(2) dynamically measuring refraction and aberrations of bare eye, both on-axis and off-axis, with the multi-axis instrument;
(3) dynamically measuring an eye with patient's existing contact lens (if any) with the multi-axis instrument;
(4) analyzing the measured data to calculate one or more off-axis refraction profiles (Sphere, Cylinder, and Axis, and/or higher order aberrations);
(5) selecting a trial contact lens based on measured off-axis refraction profile(s);
(6) putting a trial contact lens with fiducial marks on the eye;
(7) measuring the eye with the trial fiducial contact lens in place;
(8) analyzing measured data to determine misalignments (centration and/or rotation) of trial fiducial contact lens, if any;
(9) determining if a desired off-axis refraction profile was achieved;
(10) adjusting contact lens selection, and repeating steps (1) through (9), as often as needed;
(11) If necessary, due to contact lens centration offsets, designing a wavefront-guided (WFG) customized contact lens that will deliver the desired off-axis refraction profile; and
(12) measuring the progression of myopia over a long period of time.

Another factor that can be varied is the apparent distance to the visual target. The optical instruments disclosed herein can have the visual target mounted on a movable stage to provide simulated targets at different distances. Myopia progression is stimulated by near work, so it is useful to measure the off-axis refraction profile at a variety of near-work conditions, in addition to making measurements when the patient eye is focused at a far point.

An alternate workflow would be to skip the step (2) of measuring the bare eye and/or existing contact lens and go straight to measurement of the eye with a trial lens that already has a myopia progression treatment profile designed into it.

The importance of Step (2) is easy to overlook, however. Since the patient came to the doctor for treatment of myopia progression, we know the off-axis refraction profile present is one that is related to myopia progression. It would be advantageous to also conduct research studies of people who are not experiencing myopia progression for comparison purposes. The goal would be to see if off-axis refraction profile, by itself, is causative of myopia progression or if other factors are involved. In either case, existing data indicates contact lenses that affect off-axis myopia progression are effective when ideally-matched to an eye. One of the problems holding back progress on myopia progression is the small data sets available for analysis. An easy-to-use, and low-cost wide-field optical instrument that could be deployed in hundreds of clinics would enable collection of a large data sets. "Big Data" analysis techniques could then be applied to determine causes and improve treatments of myopia progression.

The software package can also evaluate the dynamic stability of the contact lens on the eye. When an eye blinks, the contact lens shifts its position and the off-axis refraction profile changes. Some lenses will stabilize on the eye faster than others. A design that stabilizes quickly for one person may stabilize more slowly on another. If the lens stabilization is slow, or variable, the intended therapeutic effect of the lens can be lost.

A second example of a workflow below describes dynamic measurements of contact lens wear to evaluate contact lens (CL) performance and to guide CL selection:

1. Measure dynamic refraction and aberrations of bare eye with multi-axis instrument;
2. Measure dynamic refraction and aberrations with patient's existing contact lens (if any);
3. Analyze measured dynamic data to calculate off-axis refraction profile(s);
4. Plot off-axis refraction profile(s) versus time;

5. Calculate and plot a difference between an intended profile and an achieved profile versus time; and calculate percentage of time that the intended profile is achieved;
6. Select a trial contact lens based on measured off-axis profile(s);
7. Put trial contact lens with fiducial marks on eye;
8. Measure dynamic data with trial fiducial contact lens in place;
9. Analyze data to determine centration/rotation of trial fiducial contact lens, and plot results versus time;
10. Analyze data to determine off-axis refraction(s) and plot results versus time;
11. Analyze data to determine a difference between a desired off-axis refraction profile and the measured off-axis refraction profile, and plot difference versus time;
12. Determine percentage of time the desired off-axis refraction profile was achieved;
13. Adjust contact lens selection and repeat steps 8-12 as often as needed; and
14. If necessary, due to contact lens centration offsets and/or rotations, design a WFG customized contact lens to fit on eye that will deliver the desired off-axis profile.

Note: the phrase "refraction profile" refers to the set of three numbers: Sphere(S), Cylinder (C) and Axis (A) of the eye being examined. The two sets of procedures above describe the dynamic evaluation of myopia control contact lenses. These procedures can also be applied to dynamic evaluation of wavefront-customized contact lenses. Evaluation of contact lens stability and centration/rotation is the same, but the desired figure of merit is the optical quality of vision achieved in the latter case (instead of the off-axis refraction profile in the former case).

Some researchers have found a correlation between myopia progression and slow accommodative responses. A useful evaluation of the suitability of a myopia control contact lens may include performing the following steps:
1. For a bare eye, measuring a dynamic accommodative response to step changes in an apparent distance to the video fixation target;
2. fitting a myopia control contact lens and re-measuring the dynamic accommodative response to step changes in the apparent fixation target distance; and
3. predicting an effectiveness of the myopia control contact lens based on changes (relative to the bare eye response) in the speed of the accommodative response relative to the bare eye's response (or simply to the accommodative response speed with the myopia control contact lens).

Accommodative responses are often considered to have a slow response, but there are also accommodative tremors that are of small magnitude and occur at rates that require fast cameras to see, for instance, at a rate of 60 hertz or greater. Some reports have indicated unusual patterns of accommodative eye tremors in eyes suffering from myopia progression, particularly in response to changes in visual inputs, such as following moving targets or switching gaze angles.

Unusual eye pursuit movements and saccade have also been reported in response to following moving targets and switching of gaze angles. So, an example of a process of evaluating the suitability of a myopia control contact lens may include doing the following steps:
1. For a bare eye, measuring a dynamic accommodative response or saccades to changes on a video fixation target that may include: (a) smooth motions of an object, and/or (b) steps changes in the object's location;
2. fitting a myopia control contact lens, and then re-measuring the dynamic accommodative response or saccades to changes in a video fixation target that may include (a) smooth motions of an object, and/or (b) step changes in the object's location; and
3. predicting an effectiveness of the myopia control contact lens based on changes (relative to the bare eye's response) in dynamic accommodative response or saccades to changes in a video target that may include (a) smooth motions of an object, and/or (b) steps changes in the object's location.

The video fixation target can be mounted on a movable electromechanical stage, to allow for changes in the target's position from near to far during a measurement sequence. The use of a second camera to measure binocular eye vergence may also show relationships to effectiveness of myopia control contact lenses.

Figure 2A:
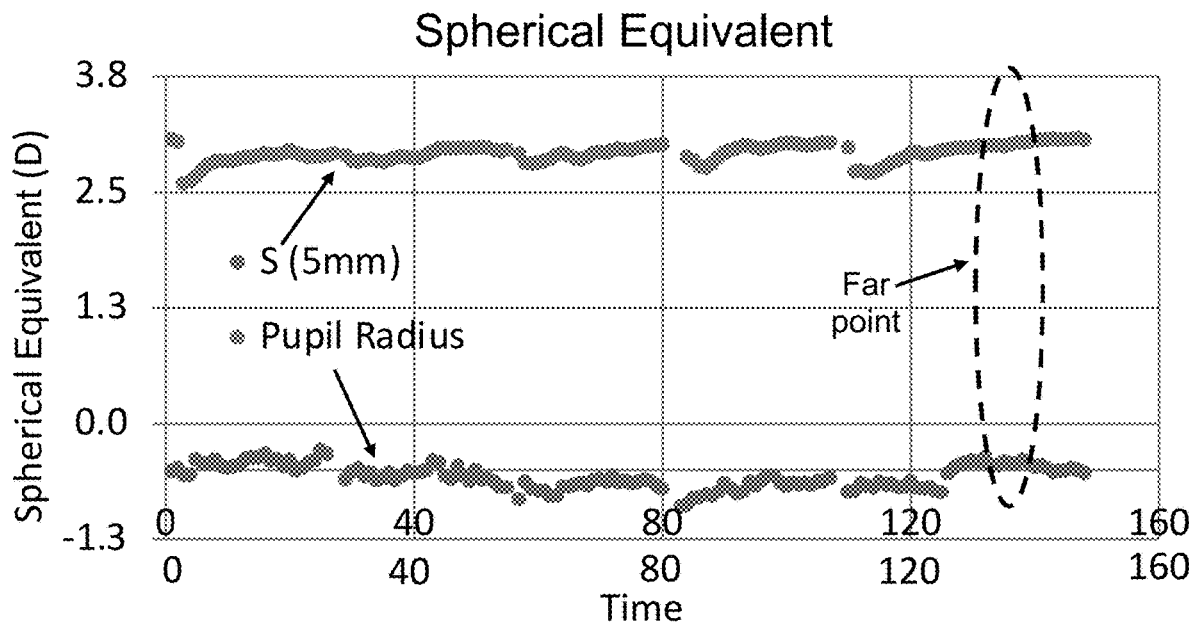
FIG. 2A shows a dynamic measurement of the spherical equivalent, and the pupil's radius, of a patient's eye, according to the present invention.

FIG. 2A shows a dynamic measurement of the spherical equivalent, and the pupil's radius, according to the present invention.

Figure 2B:
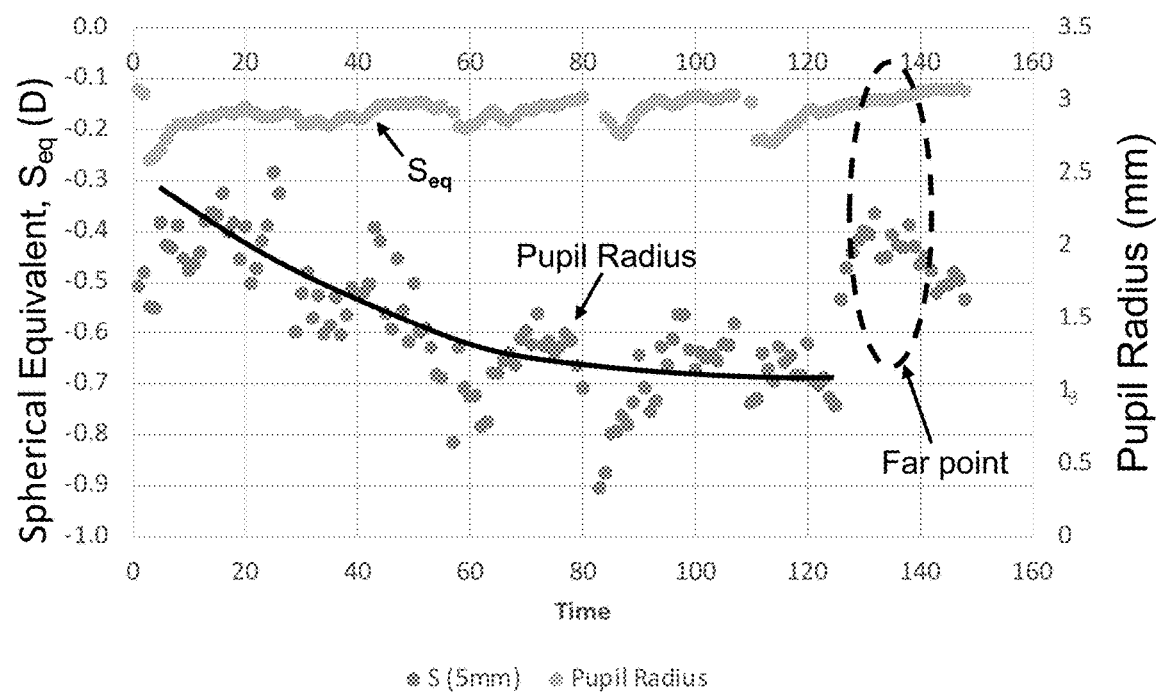
FIG. 2B shows a dynamic measurement of the spherical equivalent, and the pupil's radius, of a patient's eye, according to the present invention.

FIG. 2B shows another dynamic measurement of the spherical equivalent and the pupil's radius, according to the present invention. The pupil's radius decreases from 2.5 mm to 1 mm during the measurement sequence as the patient's focus adjusts from far to near (due to moving the video fixation target). Concurrently, the eye's refraction reduces from −0.3D to −0.1D as the pupil's radius decreases. Also, the Sphere Equivalent ($S_{eq}$) increases as the patient's focus adjusts from near to far point. Note that $S_{eq}=S+C/2$, where S=sphere and C=cylinder.

Figure 3:
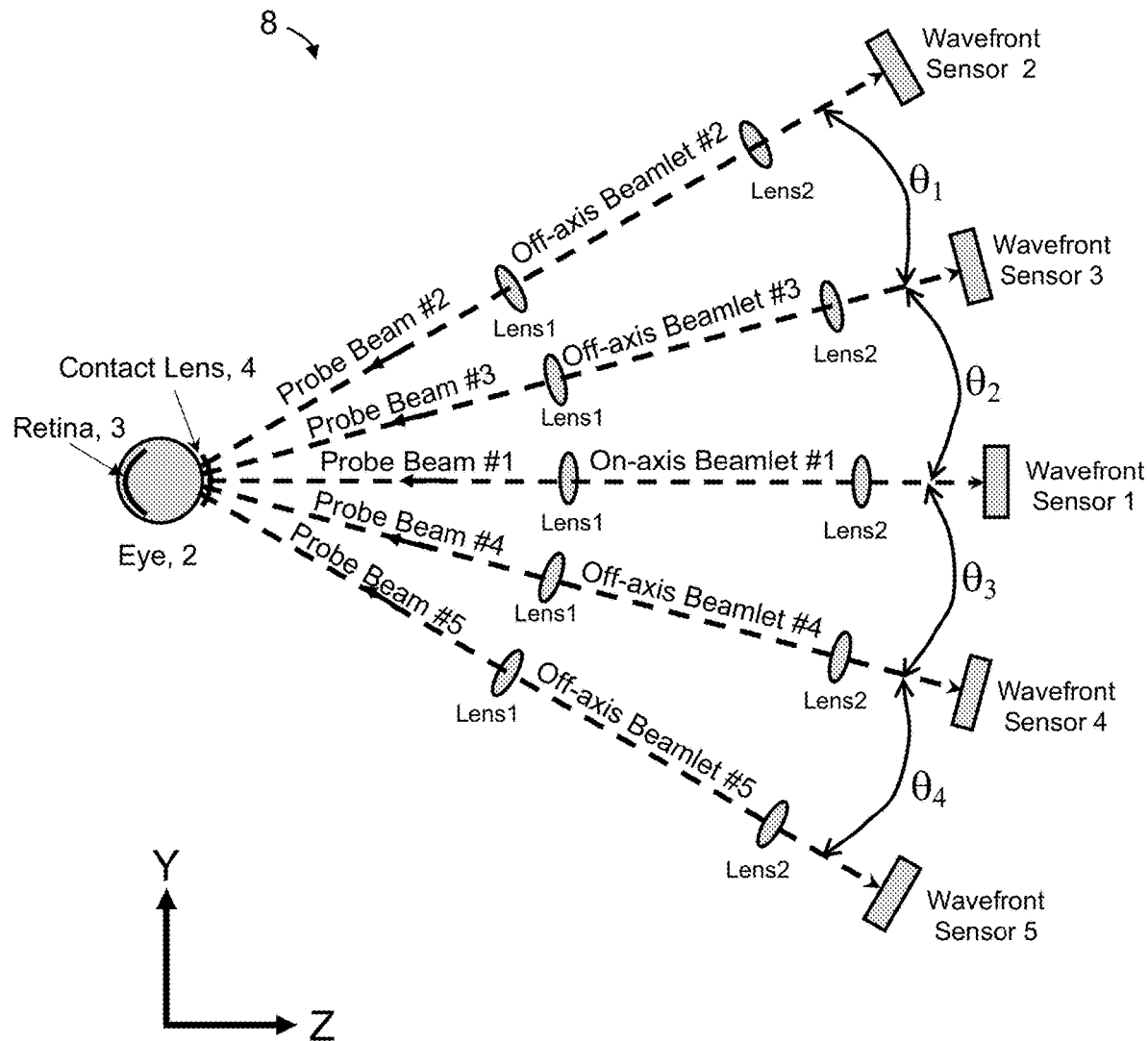
FIG. 3 shows a schematic optical configuration of a first embodiment of the present invention.

Specific Examples of a Multi-Axis Optical Instrument:

FIG. 3 illustrates a schematic optical layout of a first embodiment of a multi-axis optical instrument 8. In FIG. 3, in its most basic form, optical instrument 8 comprises five optical beamlet paths (Beamlet #1, Beamlet #2, Beamlet #3, Beamlet #4, and Beamlet #5) that are directed toward the eye (one beamlet on-axis, and four beamlets off-axis) and have a converging "fan" shape where all of the off-axis beamlets are spread out at a distal end, and they converge to a single location on the eye at a proximal end. Each beamlet is angularly separated by an angle ($\theta_1$, $\theta_2$, $\theta_3$, $\theta_4$), which can be the same as each other, or all different. In the case where ($\theta_1=\theta_2=\theta_3=\theta_4=\theta$), the same angle $\theta$ can range from 5° to 30°; and is preferably equal to 15° (see FIG. 4). Additionally, each beamlet (on-axis and off-axis) comprises their own pair of front lens (Lens1) and a rear lens (Lens2), and a wavefront sensor.

Figure 4:
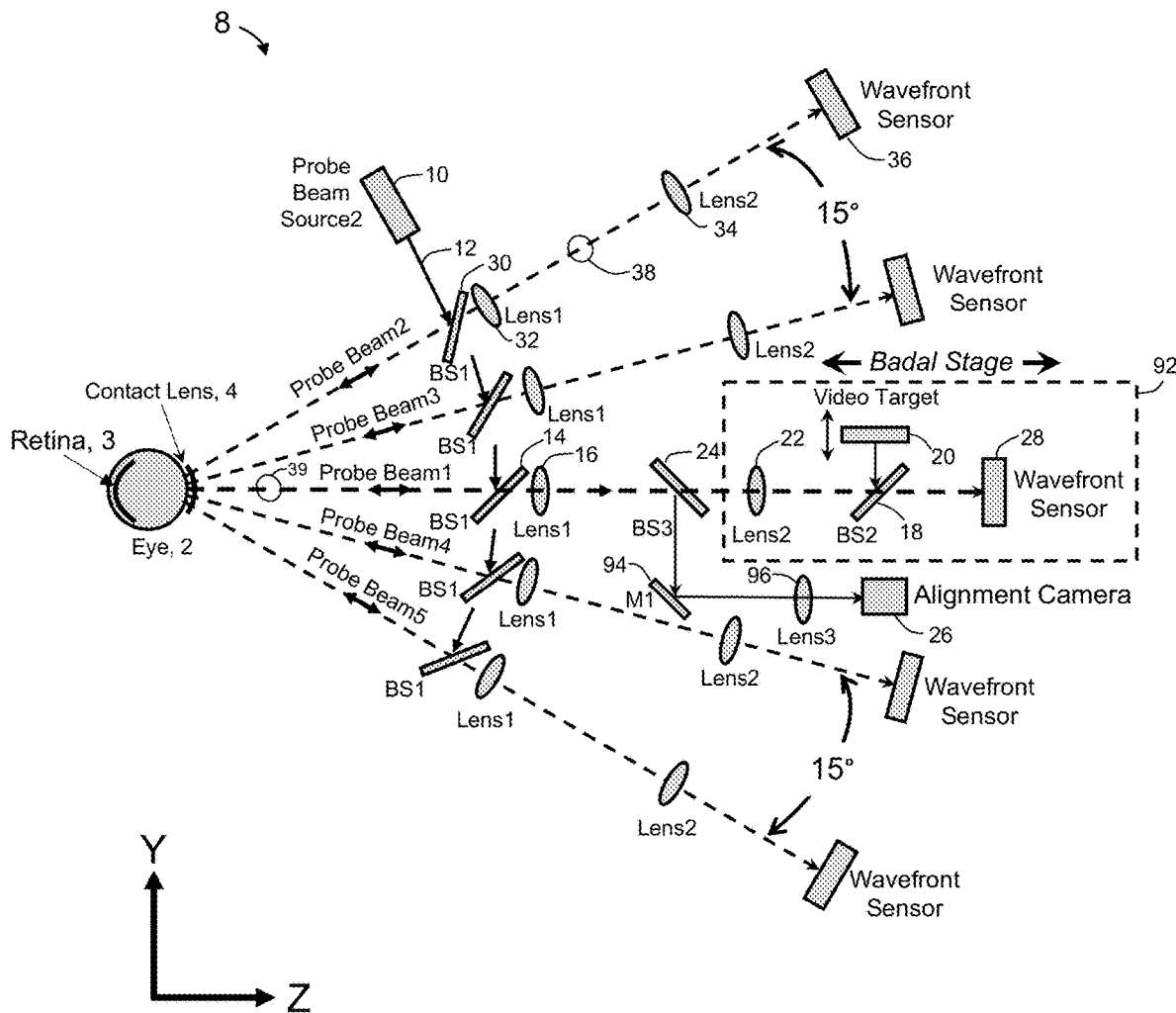
FIG. 4 shows a schematic optical configuration of the first embodiment of the present invention, with additional optical elements added.

In FIG. 4, for the first embodiment, each of the five beamlets 38, 39, etc. has their own optics to inject a probe beam 12 from a probe beam source 10 (which can be a laser source, a LED, or a Superluminescent LED (SLD), with a wavelength ranging from 780 nm to 900 nm, and is typically around 850 nm) that creates a scattering source of light on the retina. Each beamlet #1, 2, 3, 4, 5 has its own probe beam source 10, its own probe beam 12, its own front lens 32 (e.g., lens1), its own rear lens 34 (e.g., lens2), and its own beamsplitter 14 or 30, which can be operated independently of the other beamlets; or operated simultaneously with the other beamlets. The thick arrows indicate separate probe beam optics being directed by a beam splitter 14 in front of the front lens 16 (Lens1) for each optical path. FIG. 4 appears crowded with the probe beam section potentially obscuring a nearby lens of the adjacent optical path, but that is only because the optical layout is drawn on flat paper. In an actual real instrument, the beam splitter would reflect light from probe beam source 10 out-of-the-plane of the paper to avoid mechanical interferences.

In FIG. 4, a practical multi-axis instrument 8 can include an alignment camera 26 on the main axis so that an operator can align the instrument to the eye 2. The same camera 26 is capable of dynamically measuring the location of a contact lens 4 on the eye to evaluate XY centration, rotation, and stability effects. The alignment camera 26 uses a beam splitter 24 (e.g., BS3) in the on-axis path 39 to send a portion of the light via a first mirror 94 (e.g., M1) and a third lens 96 (e.g., lens3) out of the plane of the paper and onto the alignment camera 26 (which can be an infrared-sensitive camera). A practical instrument 8 can also include a video fixation target 20 for the patient to view during measurements. The apparent distance of the video target 20 can be adjusted by adjusting the target's position by operating an electromechanical stage (not shown), so that measurements of off-axis refraction can be related to near-work and far vision conditions. At one focal length from the lens, the video target 20 would image at infinity. If it is moved to a different position (further away) it would correspond to some finite distance less than infinity. Thus, we can present a target at a "near" distance (such as 40 cm), or at a "far" distance, just by moving the electromechanical stage a few millimeters.

Some researchers have obtained results indicating that five measurement paths are about ideal, with measurements taken at +30°, +15°, 0° (on-axis), −15° and −30°. So, an instrument with five optical paths is preferred. More optical paths might provide some additional benefit, but it is likely the additional benefit would be minimal (i.e., and with diminishing returns of a cost/benefit ratio).

The first embodiment of the multi-axis optical instrument shown in FIGS. 3 and 4 is particularly suited for low cost. The lenses (Lens1 and Lens2 on the off-axis beamlets 38, etc.) can all be singlets, not doublets. However, lens 18 (Lens1) and lens 24 (Lens2) on the main optical path 39 are preferably higher-quality doublet lenses with reduced distortion. The probe beams 12, 12', etc. can be generated from a laser, LED, or SLD source(s). There are no back reflections in the system, since the beam injection occurs in front of the lenses. For the purposes of simply measuring refraction, lenslet arrays inside the wavefront sensor 28 itself can be low-cost, plastic-molded products. Also, the cameras 26, 28, 36 themselves can be low-cost models with low resolution. The entire optical system can be made from one piece with no adjustments needed for front and rear lenses 16 and 22, and beam splitters 14, 18, and 24. A disadvantage is that the four off-axis wavefront sensors 36, etc. do not cover the entire range of myopia and hyperopia refractions that a bare eye can exhibit. But that is not a problem for eyes that are wearing contact lenses, because in that condition the patient's vision is nearly ideal (i.e., emmetropic).

In FIG. 4, the on-axis optical path 39 can additionally comprise a motorized Badal optometer stage 92, in order to cover the full range of hyperopes, emmetropes and myopes so that a doctor can measure base refractions for all patients. However, the main use of the off-axis paths 38, etc. is to measure the off-axis refractions when a myopia control contact lens is on the eye. So, the off-axis optical paths 38, etc. can cover a smaller range than the on-axis path and they do not need to use a motorized Badal stage 92. This can also result in a lower cost and smaller, more compact instrument.

FIG. 4 shows one possible arrangement of a motorized Badal stage 92 that comprises: video target 20, rear lens 22 (Lens2), beamsplitter 18 (BS2), and wavefront sensor 28. The use of a movable Badal stage 92 is to introduce defocus in a controlled way along the main optical path 39. It can use a set of adjustable prisms, but one can also move the rear lens 22 relative to the front lens 16 (or visa-versa) by putting these optics on a unitary, movable electromechanical platform 92. The typical arrangement of a Badal stage 92 is to use two lenses, f1 and f2. Nominally they are spaced f1+f2 apart for infinity focus (i.e., no power to the optical system). Typically, the object (eye 2) is placed a distance=f1 away from the front lens 16, and the sensor (wavefront sensor 28) is placed a distance=f2 away from the rear lens 22. With this arrangement, the eye is imaged onto the wavefront sensor 28 with magnification=$-f2/f1$. The defocus is $=d/(f1^2)$, where d is the distance the stage 92 has moved from its nominal position, f1+f2. This arrangement is useful because it maintains a desirable imaging condition, while allowing for controlled, variable defocus.

The Badal stage 92 is used to compensate for the large amount of defocus that can be present in the eye. The main aberrations of the eye are (a) defocus (in the range of −16D to +12D), (b) astigmatism (up to 8D) and (c) higher orders (normal is <0.25 micron RMS, but this can be 2.0+ micron RMS for keratoconus patients). The Badal stage 92 is used to compensate for the defocus by matching the Badal position to the defocus in the eye. This reduces the total amount of aberrations that have to be measured with the WaveFront Sensor (WFS), and it just requires that the software keeps track of how much refraction has been subtracted to determine the true refraction.

In FIG. 4, the front lens 16 and rear lens 22 form a telecentric teleobjective (not identified), which is well-known in the art. The multi-axis instrument 8 can further comprise one or more "telecentric stops" (not shown) on any (or all) of the beamlets (on-axis and off-axis) to limit the angle of rays that pass through the optics. In this arrangement, the telecentric stop is sized to clip any deviated rays above some certain threshold. With the wavefront sensor, this corresponds to limiting the motion of a spot to a specified travel, hence we use the term "Range Limiting Aperture (RLA)". This has the effect of limiting the range of travel of the focal spots inside the wavefront sensor to within some acceptable range, so that there is no confusion of information on the sensor.

A variety of different arrangements that achieve the same effect are possible. One inventive aspect of this disclosure is the arrangement of the wavefront sensors and probe beams in relation to measuring a contact lens on the eye.

Beam-combining optics could be designed to direct the gaze of a single wavefront sensor 28 and probe beam source 10 through each of the five "Lens1" positions. Suitable arrangements could include multifaceted prisms, scanning mirrors, and digital light projectors.

Figure 5:
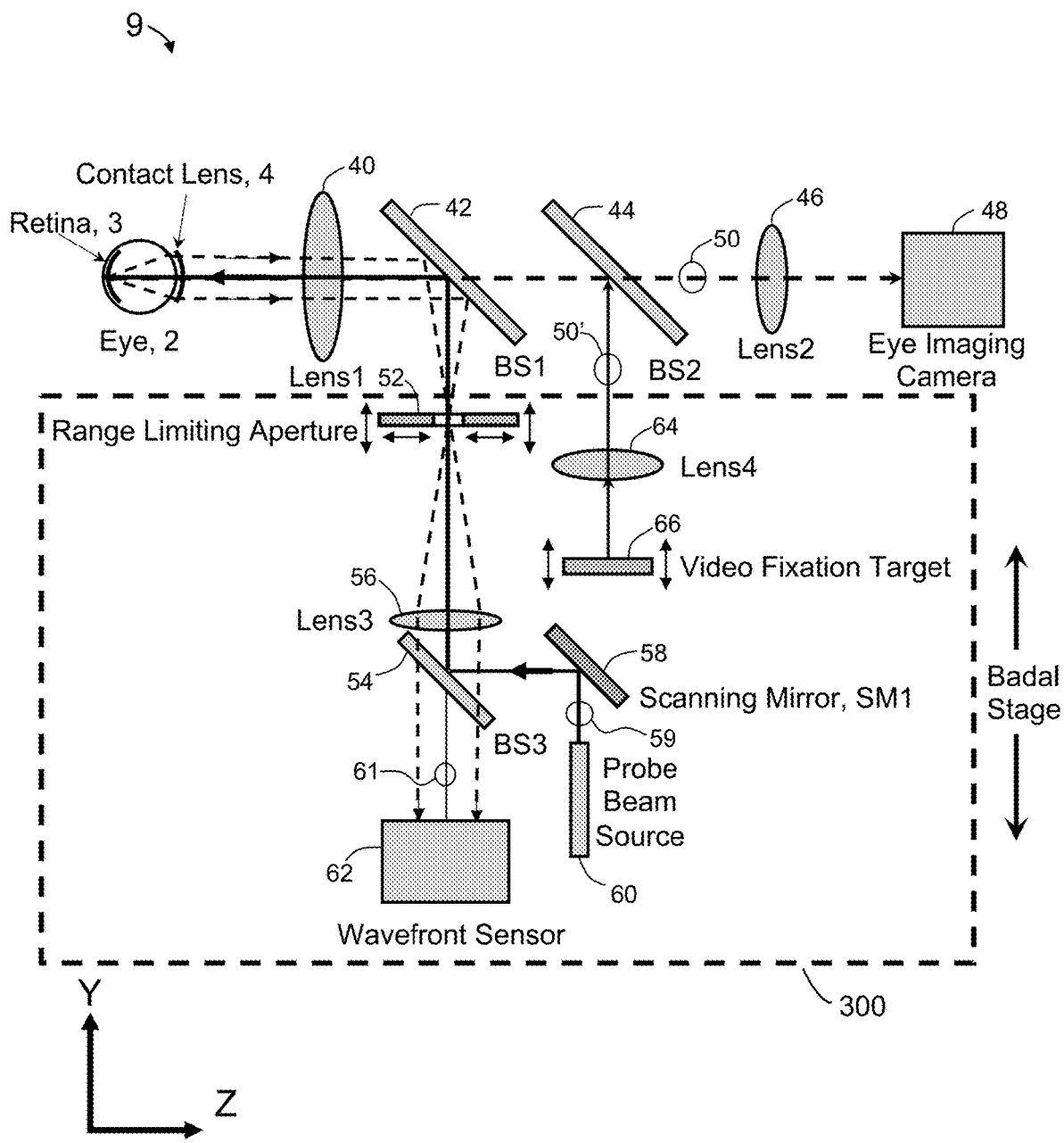
FIG. 5 shows a schematic optical configuration of a second embodiment of the present invention.

FIG. 5 illustrates an example of a second embodiment 9 of the present invention. A rotatable (scanning) mirror 58 (SM1) rotates through relatively small angles to generate multiple off-axis probe beam angles impinging on the eye 2. A single, large diameter front lens 40 (Lens1) handles most, if not all, of the off-axis paths generated by scanning mirror 58. A probe beam 59 (generated by probe beam source 60, which can be a SLD) reflects off scanning mirror 58 and then reflects of beamsplitter 54 (BS3), where it then enters lens 56 (Lens3), which focuses the light onto the center of a movable and adjustable Range Limiting Aperture (RLA) 52. Light passing through RLA 52 is redirected towards front lens 40, and then to eye 2, by first beamsplitter 42 (BS1) in a direction parallel to the direction the patient is looking. Light from probe beam 59 impinges on the retina 3 of eye 2, which scatters the probe beam light 59 back off of retina 3. The scattered light from retina 3 then goes out through the cornea and back towards the instrument 9 and eventually falls on the wavefront sensor 62 after passing through front lens 40 (Lens1), then beamsplitter 42 (BS1), then through RLA 52 and then through a third lens 56 (Lens3), and then through beamsplitter 54 (BS3), and finally on to wavefront sensor 62 as collimated rays. The wavefront path 61 of wavefront sensor 62 is oriented perpendicular to the main optical path 50. The dashed lines in FIGS. 4 and 5 show the scattered light rays emitted from the retina 3 going to the wavefront sensor 62.

Figure 6:
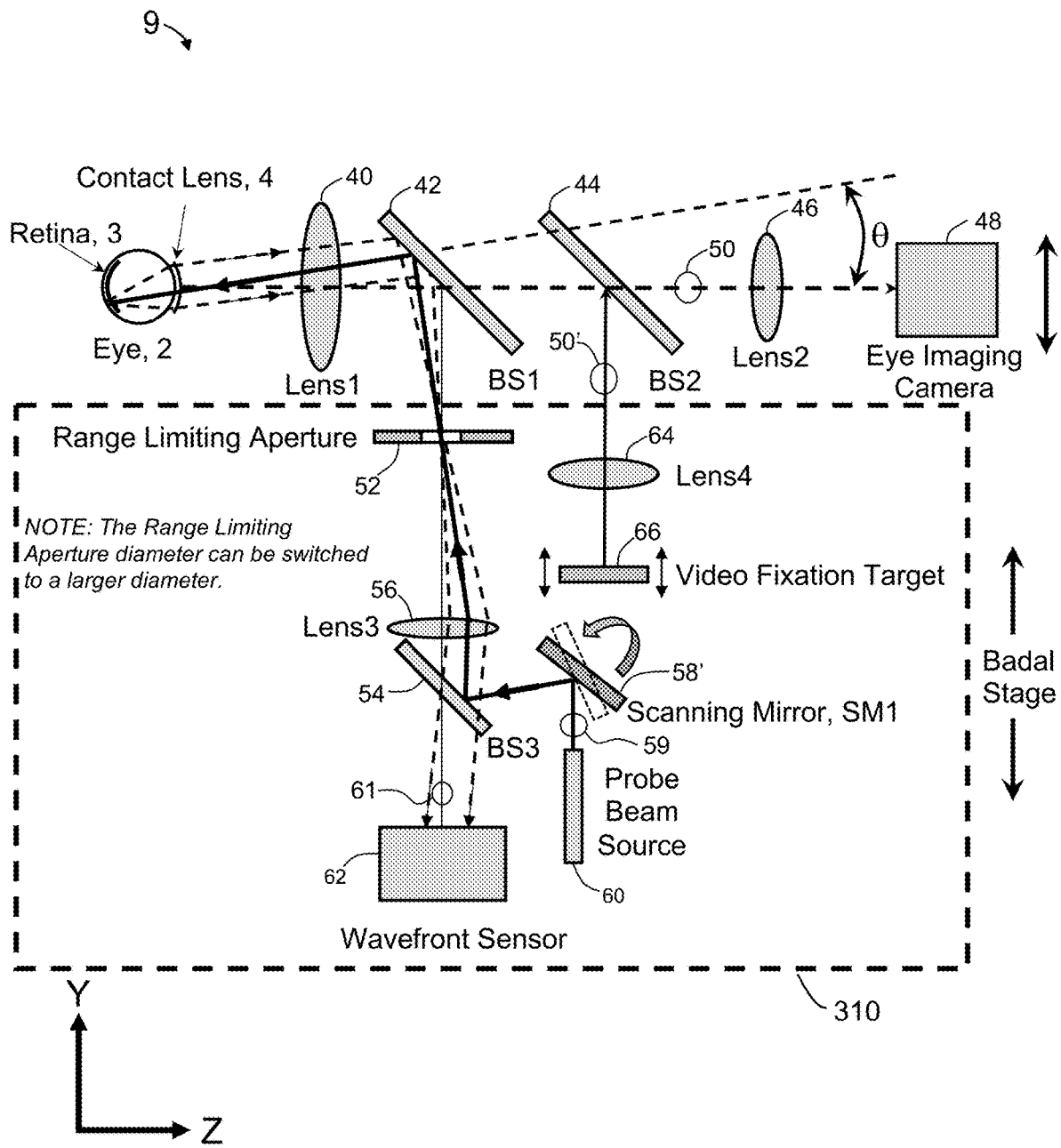
FIG. 6 shows a schematic optical configuration of the second embodiment of the present invention.

In FIGS. 5 and 6, light emitted from the Video Fixation Target 66 is focused by lens 64 (Lens4) onto a second beamsplitter 44 (BS2), which redirects the light onto the main optical path 50, which then passes through beamsplitter 42 (BS1) and then through front lens 40 (Lens1), which focuses the light onto eye 2 while passing through contact lens 4 disposed on the cornea of eye 2. Light emitted by eye 2 (including scattered light from retina 3) then goes out of the cornea back towards the instrument 9 and eventually falls on the eye camera 48 after passing through front lens 40 (Lens1), then beamsplitter 42 (BS1), then through beamsplitter 44 (BS2), then through a second lens 46 (Lens2), and finally on to eye camera 48 (which images the pupil, sclera, and eyelids). Eye camera 48, optionally, can be sensitive to infrared light. Optionally, the video fixation target 66 can be made moveable along the Y-axis (i.e., optical path 50') by being mounted on an electromechanical stage (not shown). This adjustment can change the video target's position from near to far along optical path 50', which is oriented perpendicular to the main optical path 50.

In FIG. 6, the scanning mirror 58 (SM1) has been rotated a few degrees (58') from the previous on-axis position so that the probe beam 59 now enters the eye at an off-axis angle. The required scan angle of the mirror 58 varies somewhat according to what lens focal lengths are chosen in the relay lenses. In a practical system, to get a 15° off-axis angle at the eye, the mirror would rotate 5°. So, to get a 30° degree off-axis angle at the eye, the mirror would rotate 10° degrees. To get a 40° degree off-axis angle at the eye, the mirror would rotate 13.3° degrees. Since the eye 2 has the same gaze angle as before in FIG. 5, the wavefront measurement made in FIG. 6 is an off-axis refraction.

In FIG. 5, for the on-axis measurement, the RLA 52 is centered on the instrument's main optical axis 50. For a large off-axis angle, the RLA's diameter (aperture opening) can be increased so that the beam traveling back to the wavefront sensor 62 can pass through the RLA 52 without blockage. For the on-axis measurement, the RLA 52 blocks a reflection from the cornea that can create a blob of light (reflection) on the wavefront sensor 62 that prevents making a good wavefront measurement. However, for the off-axis case with a significantly rotated mirror 58', the RLA 52 is actually not needed because the angle of light beam entering the eye 2 is such that no blob of light is created on the wavefront sensor even when the RLA 52 is not in place. The use of a moveable and/or variable-diameter RLA 52, in synchronization with making off-axis measurements, is an inventive aspect of this invention.

FIGS. 4 and 5 both show an alignment camera 26/48 that captures a regular visual image of the eye, that is used for dynamically aligning the instrument to the eye in the X-Y plane; and for dynamically measuring the misalignment (centration and rotation), and stability of a contact lens fitted on an eye. FIGS. 4 and 5 also show a moveable fixation target 20/66 for the patient to view. The fixation target can be a micro-video-display. The position of the moveable video target 20/66 can be adjusted closer or farther to the eye to stimulate near or far vision. This capability is of interest because some researchers think that differences in off-axis refraction in near and far vision is a factor that affects myopia progression. But up until now, there have been no readily-available, low-cost clinical instrument capable of collecting data to test that idea. The video target's path 50' (see FIG. 5) can comprise lens 64 (Lens4). Lens 64 (Lens4) can be more complex than a single lens (singlet). It can be a doublet lens that contains two parts: (1) an astigmatism compensation lens joined to a (2) defocus compensation lens.

In FIG. 5, a probe beam 59 from probe beam source 60 (e.g., a SLD) reflects off of rotatable scanning mirror 58 (SM1), which then is redirected by BeamSplitter 54 (BS3) through lens 56 (Lens3), where it passes through the central opening of RLA 52, and then onto BeamSplitter 42 (BS1), which redirects the probe beam 59 onto the main optical axis 50 and into the central part of eye 2.

The example of a second embodiment shown schematically in FIGS. 5 and 6 is not able to provide the very wide range of off-axis angles that can be obtained using multiple, independent optical paths (as in the first embodiment FIG. 3). However, some researchers believe that myopia progression is entirely caused by an off-axis refraction profile occurring with a 12 degree (+/−6 degrees) field about the central line of sight. A single objective lens 40 (lens1) used in front of the eye can capture data within a 20° field of view, so this second embodiment is also likely to be clinically useful. Note that the second embodiment of the multi-axis instrument shown in FIG. 5 is more compact than the first embodiment shown in FIG. 3.

Figure 7:
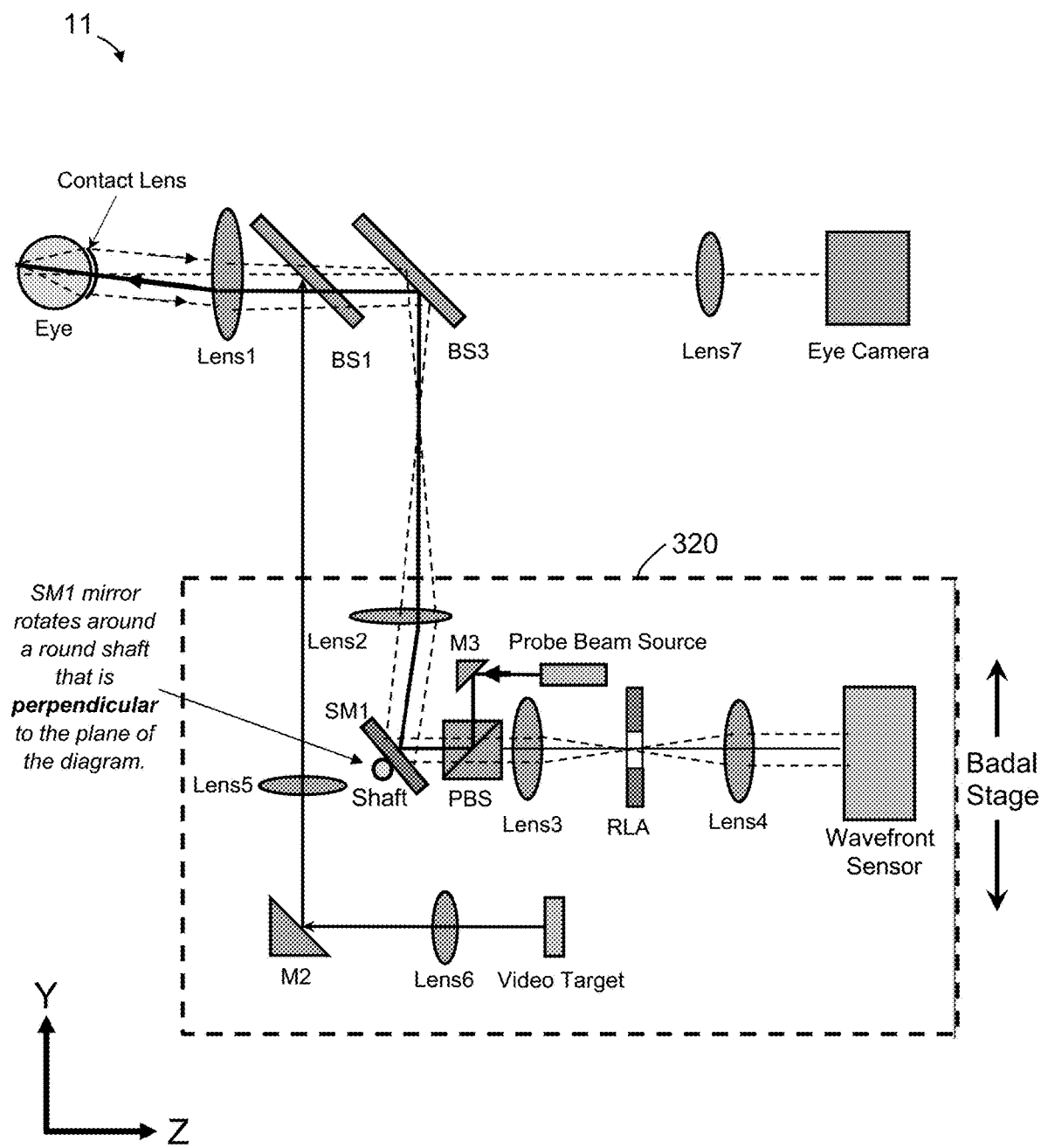
FIG. 7 shows a schematic optical configuration of a third embodiment of the present invention.

FIG. 7 shows a schematic optical configuration of a third embodiment, 11, of the present invention. The scanning mirror SM1 is one focal length from lens2, so the probe beam travels parallel to the main optical axis in between Lens2 and Polarized Beamsplitter (PBS). However, it is displaced from the main optical axis. This displacement causes the beam to exit Lens1 at an angle. The eye is also located one focal length from Lens1, so the beam enters the center of the eye. The beam travels to the retina and light scatters off the retina. The dashed lines show a beam exiting the eye and traveling to the wavefront sensor. In the space between Lens1 and SM1, the beam follows a path that is significantly displaced from the main optical axis, so the optics have to be larger than would be needed for the on-axis case. Once the beam reflects off of the scanning mirror SM1, the beam follows the same path that it did for the on-axis case and the lenses can be the same size as they were for the on-axis case. Also, the range limiting aperture RLA is in the same location as it was for the on-axis case.

FIG. 7 also shows that the scanning mirror, SM1, has rotated a small angle (<10°) about an axis that is perpendicular to the plane of the paper (i.e., scanning mirror SM1 rotates about a round shaft that is perpendicular to the plane of the diagram). This creates an off-axis scan that travels vertically up and down. Such a scan pattern is useful, but is somewhat undesirable, because the probe beam may hit the eyelashes that are above the eye. So, a vertical scan only covers a range that is somewhat less than can be attained with a horizontal scan. To produce a horizontal scan, the scanning mirror SM1 should rotate about a shaft, S, that is in line with (parallel to) the main optical axis of the instrument. This is what is shown in FIG. 5C. Note that the probe beam is first turned by mirror 3 (M3), and then is turned back into its original direction by a Polarizing Beamsplitter (PBS), before travelling on to scanning mirror (SM1).

Figure 8:
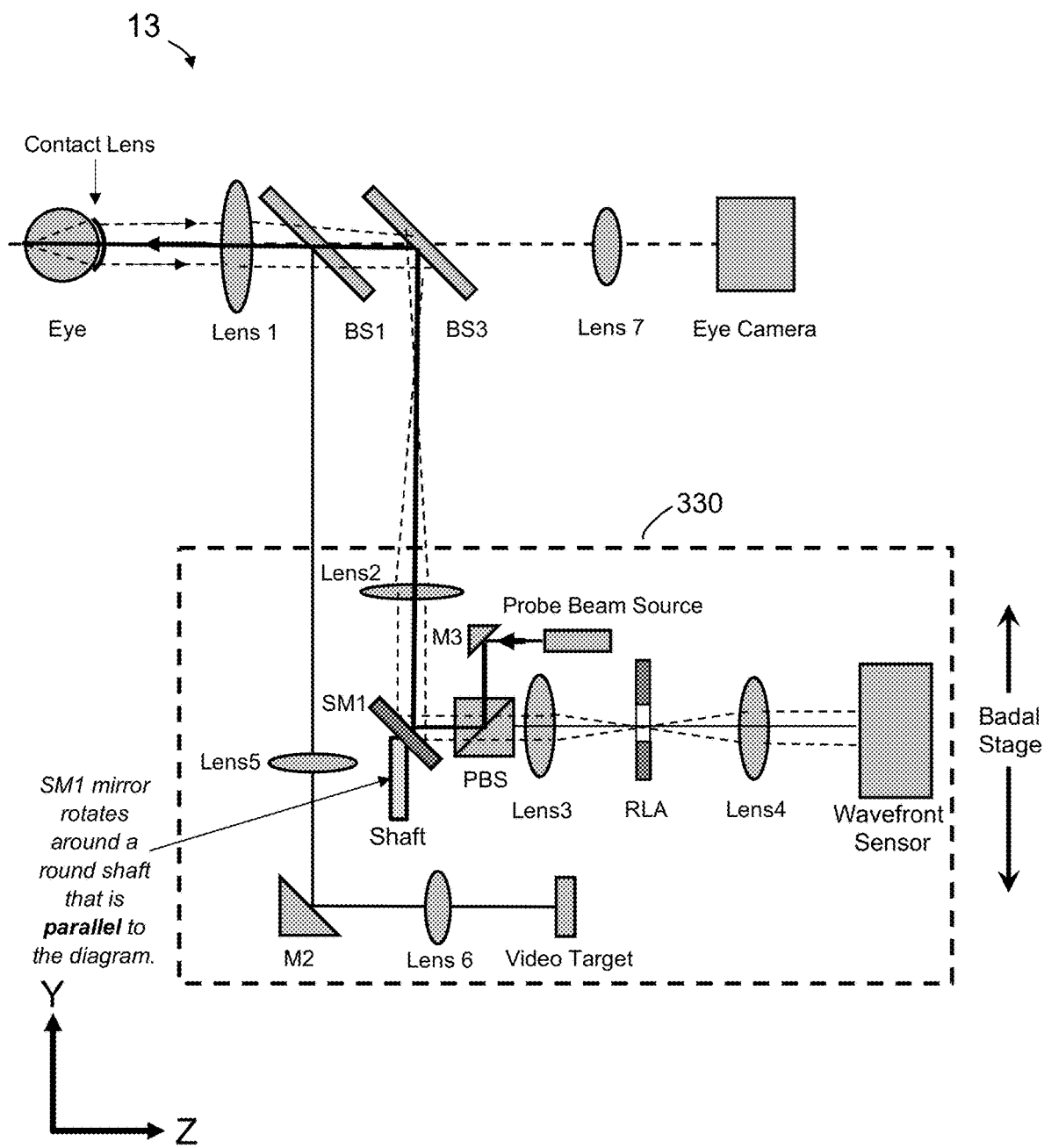
FIG. 8 shows a schematic optical configuration of a fourth embodiment of the present invention.

FIG. 8 shows a schematic optical configuration of a fourth embodiment, 13, of the present invention. In this figure, the scanning mirror, SM1, rotates about a round shaft that is parallel to the plane of the diagram. The probe beam scans in a plane that is perpendicular to the plane of the diagram, so the actual scan motion is not evident in the diagram.

Figure 9:
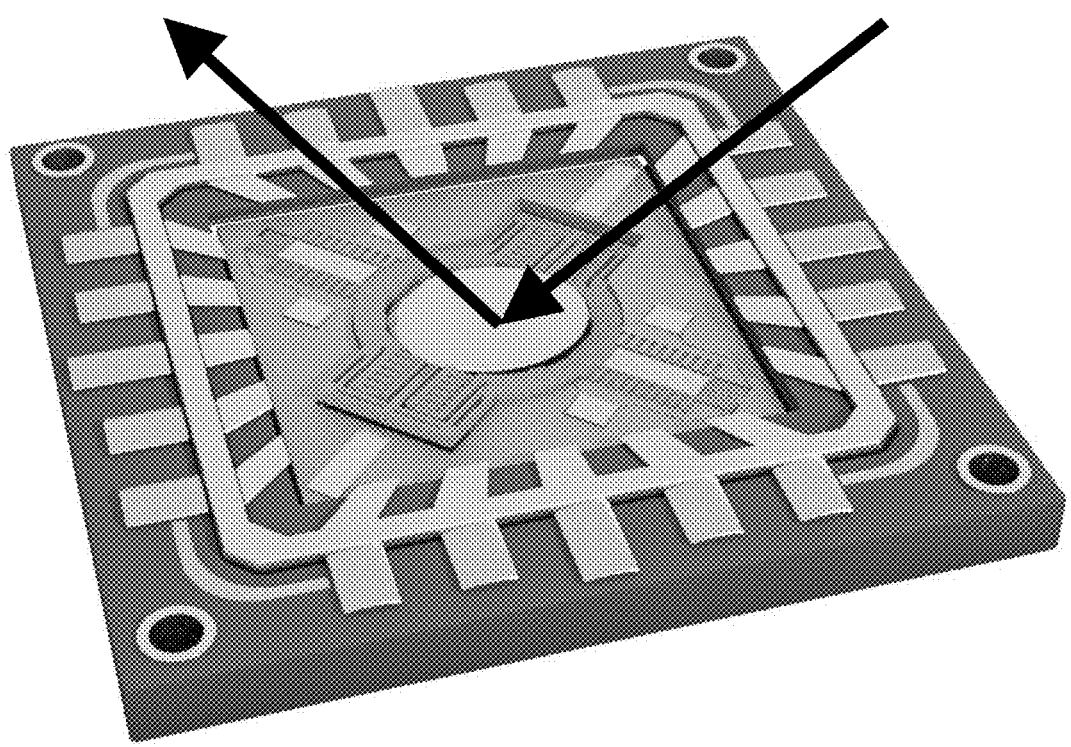
FIG. 9 shows a perspective view of an example of a 2-D MEMS scanning mirror made by Mirrorcle Technologies, Inc.

FIG. 9 shows a perspective view of an example of a 2-D MEMS scanning mirror, made by Mirrorcle Technologies. Such a 2-D MEMS scanning mirror can be used in place of a standard flat scanning mirror, SM1, in FIGS. 7 and 8, to enable scanning of the eye with the probe beam in both vertical and horizontal directions, or combinations of both directions.

It has been discussed in this disclosure that some embodiments of the instrument described are best suited for near-emmetropic vision with a contact lens on the eye. But, the off-axis wavefront sensors are also capable of measuring low myopia (and low hyperopia). That is the region of interest for younger people that are at the beginning stages of myopia progression.

The range of the off-axis wavefront sensors can be extended into the mid-myopia range by use of extended range algorithms, to further increase the usefulness of the instrument. Such algorithms allow the software to calculate accurate wavefronts even when focal spots from a particular lenslet have strayed into adjacent AOIs (Areas of Interest) that are normally associated with other lenslets. The CLAS2D software [Copyright 2020, WaveFront Dynamics Inc.] contains such algorithms, and there are descriptions of them in the CLAS2D software manual. The data collected with multiple angles can be used as input for tomographic reconstruction of internal eye structures. A US patent for that concept was issued to Dan Neal and Richard Copland, U.S. Pat. No. 6,634,750, "Tomographic Wavefront Analysis System and Method of Mapping an Optical System", which is incorporated herein by reference in its entirety.

A useful aspect of the invention in the present disclosure is that if one can build inexpensive wavefront sensors, it can result in a simpler and less expensive instrument that uses an individual, dedicated wavefront sensor for each angle of off-axis refraction being measured. Of course, that depends on having a low-cost wavefront sensor (note: concepts for those have been recently developed by Wavefront Dynamics). The multiple off-axis path wavefront sensor approach shown in FIG. 3 also has an advantage that data can be acquired on each off-axis angle simultaneously, or separately. This enables more thorough investigations of accommodation dynamics.

In FIGS. 5 and 6, like most instruments that measure the eye, there is a camera that provides an image of the eye that the operator sees while aligning the instrument. This camera is labeled Eye Imaging Camera or Iris Camera (they mean the same thing). The same camera can also measure the location of a contact lens on the eye in a dynamic fashion to evaluate centration, rotation, and stability. Also, like most instruments, there is a fixation target for the patient to view so the eye will have a steady gaze. The patient can view the target as a reflection off of the beam splitter BS2. The fixation target can be dynamically positioned to stimulate far or near vision. Some researchers think that a difference in off-axis refraction in far and near vision is a factor that affects myopia progression. But up until now, there have been no clinical instruments capable of collecting data to test that idea.

FIG. 7 shows the mirror rotated about an axis that is perpendicular to the plane of the paper. This creates a scan that travels vertically. Such a scan is useful but is somewhat undesirable because the probe beam may hit the eye lashes that are above the eye. So, a vertical scan covers a range that is somewhat less than can be attained with a horizontal scan.

FIG. 8 shows a scheme where, to produce a horizontal scan, the mirror SM1 should rotate about a round shaft that is in-line with the main optical axis of the instrument. If the mirror rotates as shown in FIG. 8, the beam angles traced at the eye are mostly horizontal, but it also moves slightly vertically. The trace is slightly curved. A typical situation is that if the horizontal scan is 15° at the eye, there is a vertical shift of 2°. This is acceptable for the purpose of prescribing myopia control contact lenses. However, end users might prefer a purely horizontal trace. One conventional solution is to have a mirror that can scan in two axes. A simplified method to attain a purely horizontal scan driven by a single scan motor is for the rotating shaft to follow a slightly curved cam or a conically tapered shaft. There are numerous schemes that can achieve that goal.

Instead of choosing between the horizontal and vertical scans, a single mirror that can scan in both angles at once can be used. A 2-D MEMs scanning mirror, such as that shown in FIG. 9, such as those made by Mirrorcle Technologies, are capable of such motions. However, they tend to have somewhat limited size and scan angles in the present commercial offerings. It is expected that in the future, mirrors with larger scan angles and diameters will become readily available.

Figure 10:
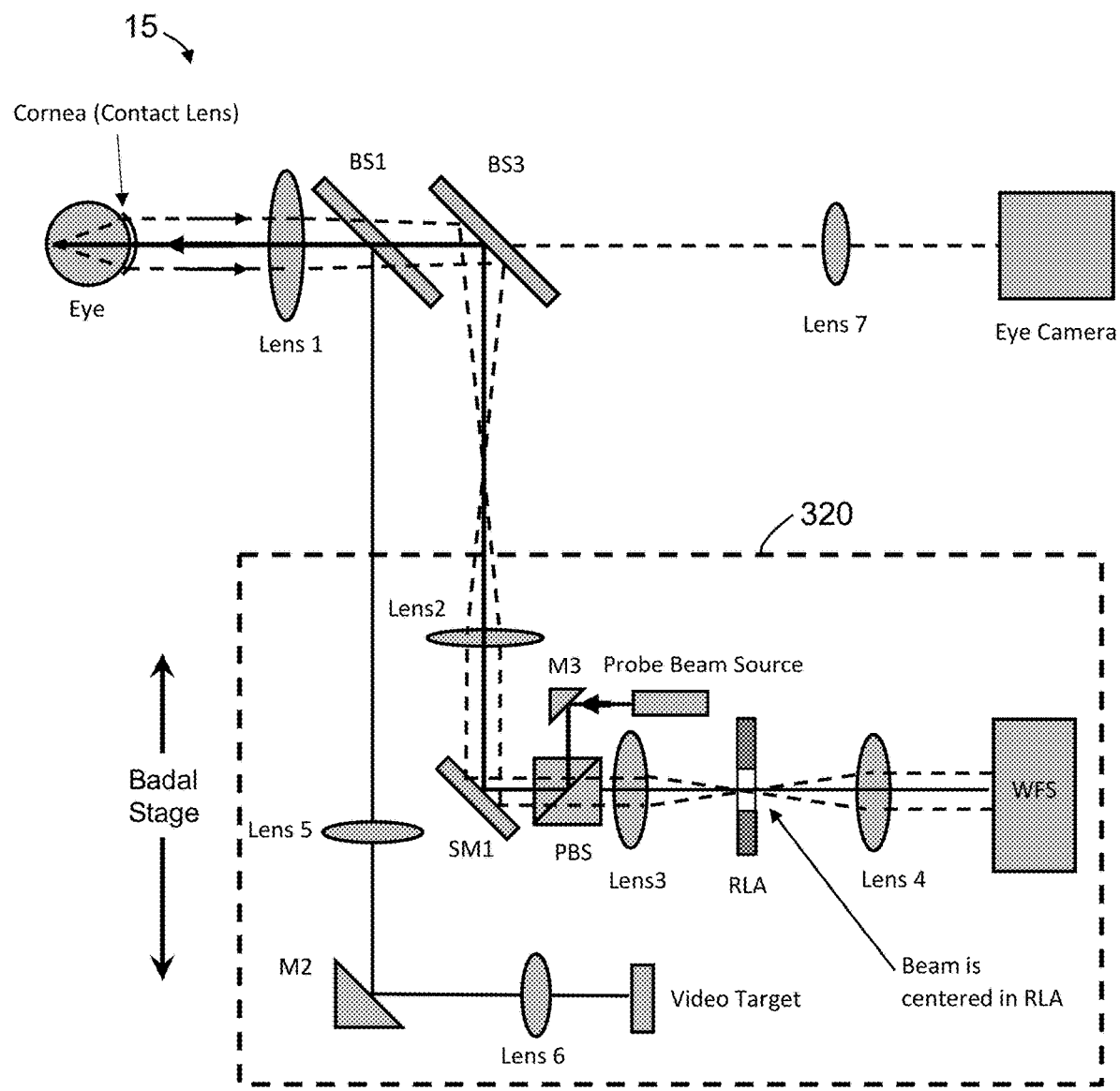
FIG. 10 shows a schematic optical configuration of a fifth embodiment of the present invention.

FIG. 10 shows another configuration for measuring the eye. The mirror M1 is set for an on-axis measurement of the eye like a normal aberrometer (iDesign™, for example). Light from the probe beam travels through the system and hits the retina. Light scatters from the retina and exits the cornea as the dashed lines indicate. Light travels through the system and reaches the wavefront sensor. Computer analysis of the image gives the refractive state of the eye. The dashed box 320 represents optics that move together as a Badal optometer to adjust for a patient's myopia, emmetropia or hyperopia.

Figure 11:
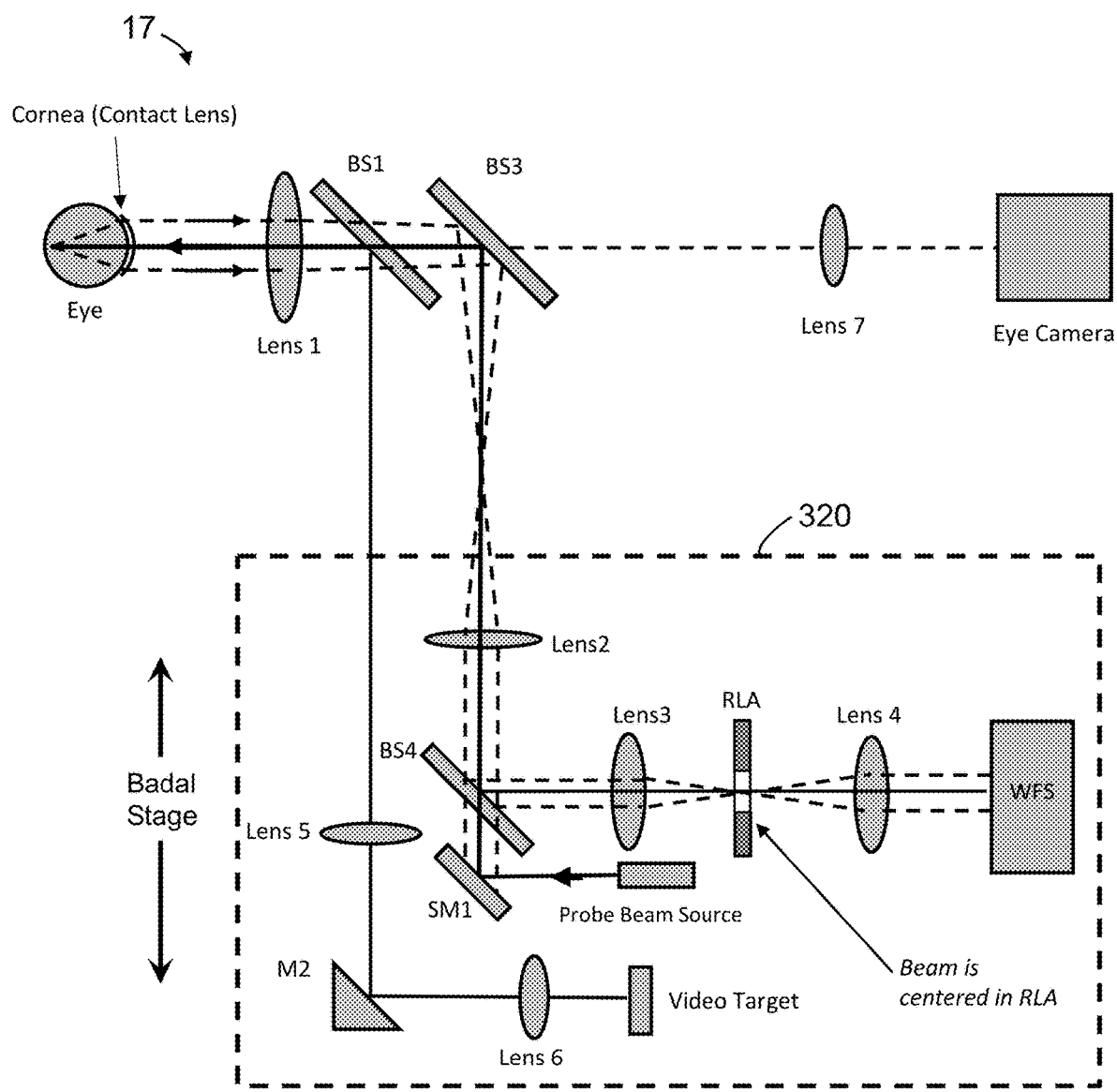
FIG. 11 shows a schematic optical configuration of a sixth embodiment of the present invention.

In FIG. 11, the scanning mirror SM1 is shown in a position that is rotated from the on-axis setting shown in FIG. 5. The mirror is one focal length from the lens L2, so the beam travels parallel to the main optical axis in between L2 and BS3. However, it is displaced from the main optical axis. This displacement causes the beam to exit L1 at an angle. The eye is located one focal length from L1, so the beam enters the center of the eye. The beam travels to the retina and light scatters off the retina. The dashed lines show a beam exiting the eye and traveling to the wavefront sensor. In the space between L1 and SM1, the beam follows a path that is significantly displaced from the main optical axis, so the optics have to be larger than would be needed for the on-axis case. Once the beam reflects off the mirror SM1, the beam mostly follows the same path that it did for the on-axis case and the lenses can be the same size as they were for the on-axis case. However, the beam's focus is moved closer to edge of the RLA and the consequences of that are discussed further with FIGS. 12 and 13.

FIG. 11 illustrates an alternative embodiment where the probe beam reflects off the mirror SM1 and then passes through a beam splitter BS4. The light beam coming back from the eye reflects off BS4 to reach the wavefront sensor. The on-axis case of eye measurement is depicted. BS4 could be partially reflecting, for example: 10% transmitting and 90% reflecting. A slightly better scheme for light efficiency would be for BS4 to be a polarizing beam splitting cube, in which case the P-polarization going through BS4 is transmitted at 99%. A quarter wave plate (QWP) in front of the eye results in S-polarized light going back into the system and S-polarized light reflects off BS4 at 99% efficiency to the wavefront sensor.

Figure 12:
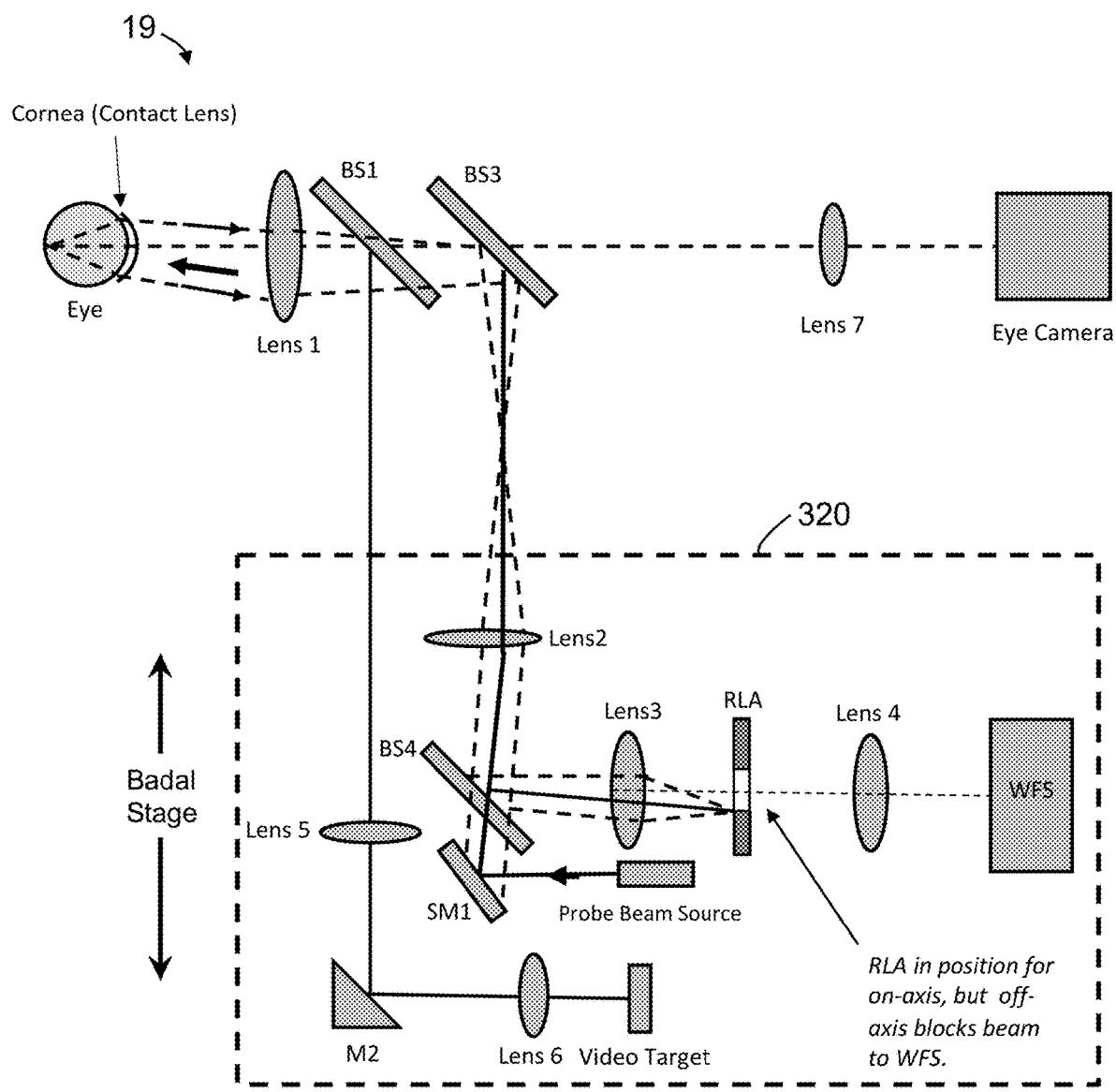
FIG. 12 shows a schematic optical configuration of a seventh embodiment of the present invention.

FIG. 12 shows the scanning mirror SM1 rotated by about 5° so that the probe beam enters the eye at an off-axis angle. The RLA is shown in position in FIG. 11 for the on-axis measurement, and the undesirable result is that the RLA blocks the beam before it reaches the wavefront sensor.

Figure 13:
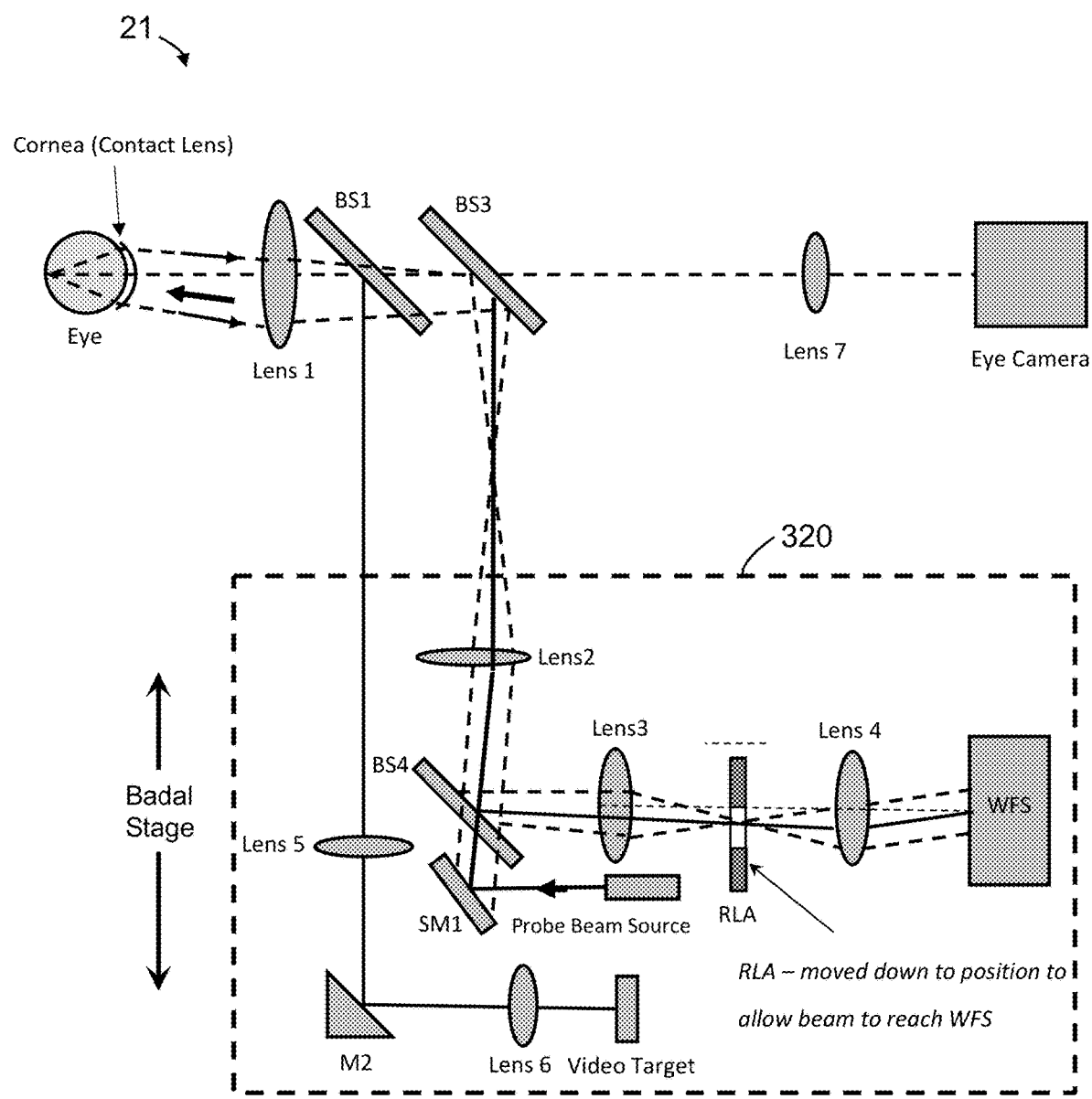
FIG. 13 shows a schematic optical configuration of an eighth embodiment of the present invention.

FIG. 13 shows that the RLA has been moved down to allow the beam to reach the wavefront sensor WFS. The ideal position is linearly dependent on the rotation angle of SM1. The mechanism for moving the RLA could be driven by the same motor that turns the mirror SM1 through a mechanical linkage. Or, it could be moved by a separate motor. Another option is to simply enlarge the diameter of the RLA with a motor-controlled variable diameter iris. A useful function of the RLA is to restrict a bright reflection that sometimes comes off the cornea and reaches the wavefront sensor when an on-axis measurement is being done. With the off-axis cases, the corneal reflection naturally deflects away from the instrument optical axis and the RLA is not needed. Enlarging or moving the RLA would be done in conjunction with extended dynamic range wavefront sensor software algorithms. Another aspect that can be seen in the figure is that diameter of the lenses needs to be slightly larger.

Figure 14:
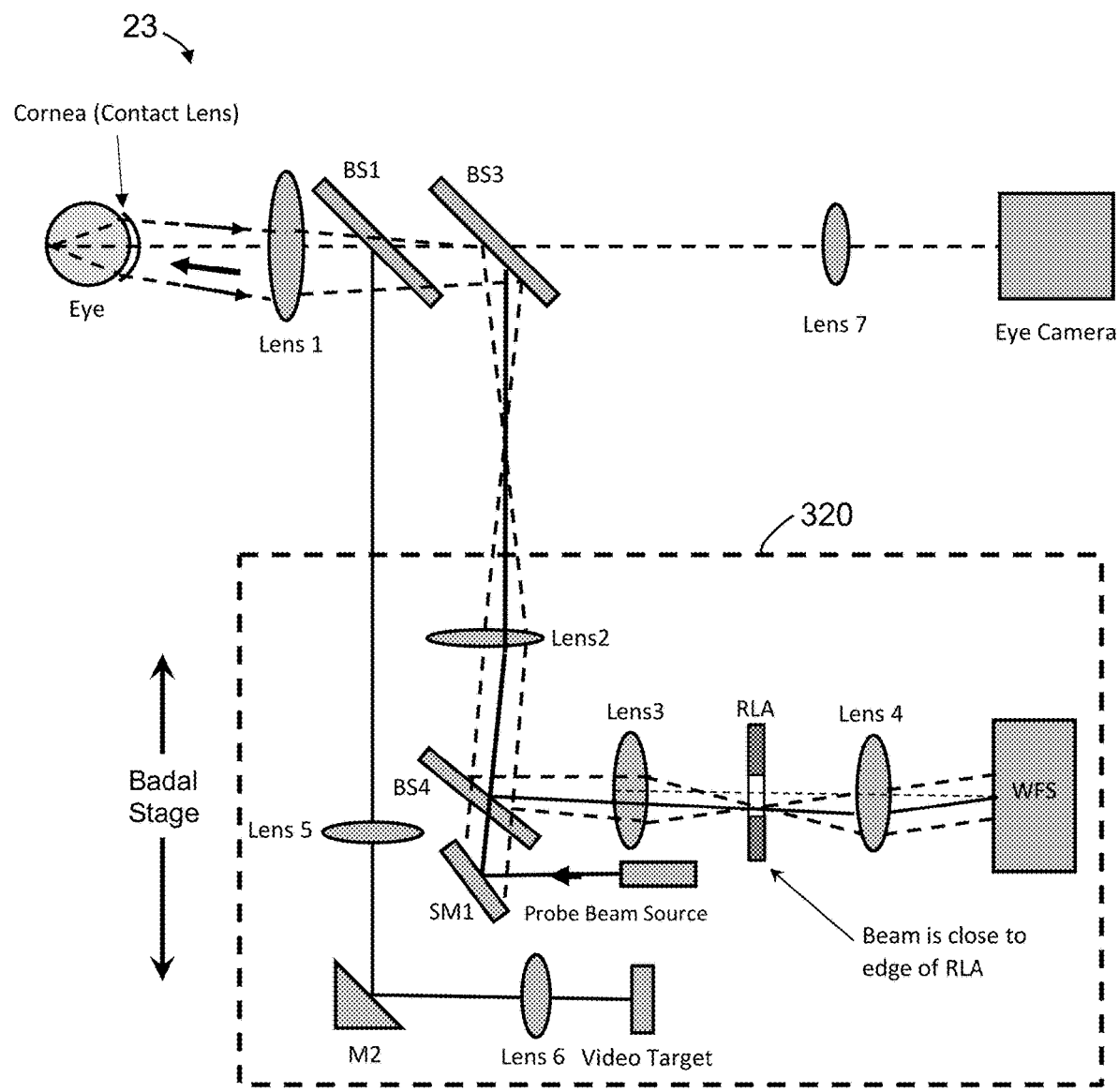
FIG. 14 shows a schematic optical configuration of a ninth embodiment of the present invention.

In FIG. 14, the fourth beam splitter BS4 rotates to compensate for the rotation of the mirror SM1 so the beam coming from the eye passes through the RLA. For example, if SM1 rotates positive five degrees, BS1 rotates negative five degrees. A single motor can drive both SM1 and BS4 by a mechanical linkage. The next section describes some general aspects concerning the use of the embodiments described above.

The process of measuring the off-axis refraction of an eye begins with the measurement of the on-axis refraction, when the scanning mirror SM1 sends the probe beam along the central optical axis of the instrument. Then the mirror rotates to a desired angle, stops, and then the next wavefront measurement is made. Typically, measurements would be made at 5-7 different angles. The entire set of measurements can be completed within 0.2 seconds so the eye would not be able to move in between measurements.

The expected method of using a rotatable mirror is that it stops at distinct angles for each refraction measurement. A typical time the mirror might be stopped is about 20 milliseconds. An alternate setup is that the mirror rotates at a constant rate and the wavefront sensor takes synchronized images over a very short time period, for example one millisecond. This might allow the measurement process to be completed even more quickly. It would require flashing the probe beam in synchronization with the image acquisition timing.

The range of horizontal scan attainable is primarily set by the size of the optics in the beam train. Practical calculations show that if the lens L1 has a focal length of 73 mm and a diameter of 32 mm, there is a range of 14 degrees on the wavefront sensor. So, if the eye looks straight into the instrument at a centered image on the video target, the instrument can measure off-axis refractions over the range of +7° to −7°. A simple way to extend the total off-axis range is to take advantage of the fact that the image shown on the video display target can be shifted. If the center of the image is moved over to the left by five degrees, and a scan is done, the range covered would be +12° to −2° of off-axis refraction. Similarly, a right shift of the target makes the scan cover +2° to −12°. Potentially, there could be some difference in the eye's accommodation between the three different scans. The overlapped region in the center allows a single, combined off-axis refraction plot to cover from −12° to +12° for a total scanned range of 24°. Similarly, the video fixation target can be shifted vertically, so that the scan process creates a surface rather than just a slice.

Figure 15A:
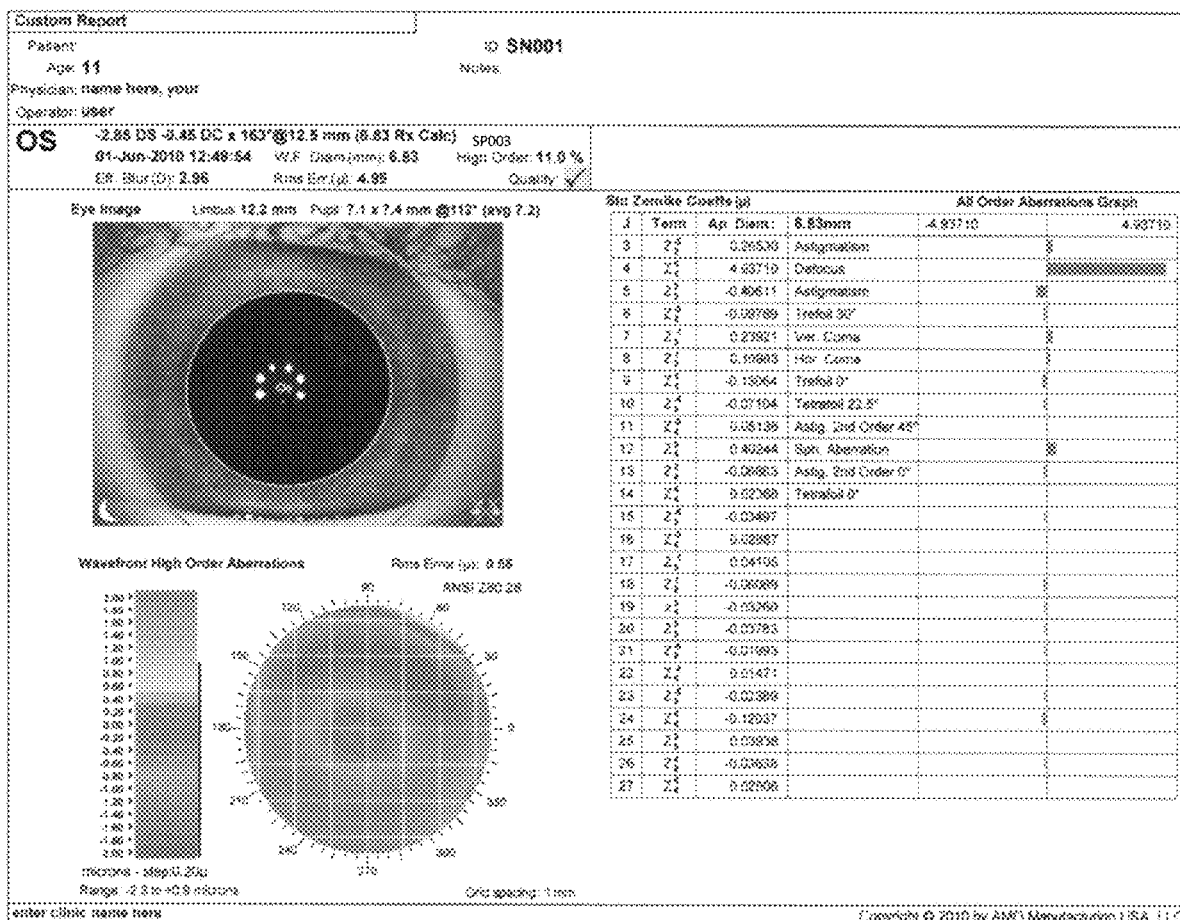
FIG. 15A shows a snapshot of a computer screen showing results of (1) a visual image of the patient's pupil, (2) a contour plot of wavefront measurements, and (3) a table listing the Zernike coefficients for the first twenty-seven Zernike polynomials, for a patient's bare eye, according to the present invention.

FIG. 15A shows a snapshot of a computer screen showing results of: (1) a visual image of the patient's pupil, (2) a contour plot of wavefront measurements, and (3) a table listing the Zernike coefficients for the first twenty-seven Zernike polynomials, for a patient's bare eye, according to the present invention. FIG. 6A is an example of a young subject's bare eye (age 13) that has presented with a modest amount of myopia. Note that there is a considerable amount of spherical aberration (defocus) present ($Z_2^0$ coefficient), and the RMS value=4.9 microns.

Figure 15B:
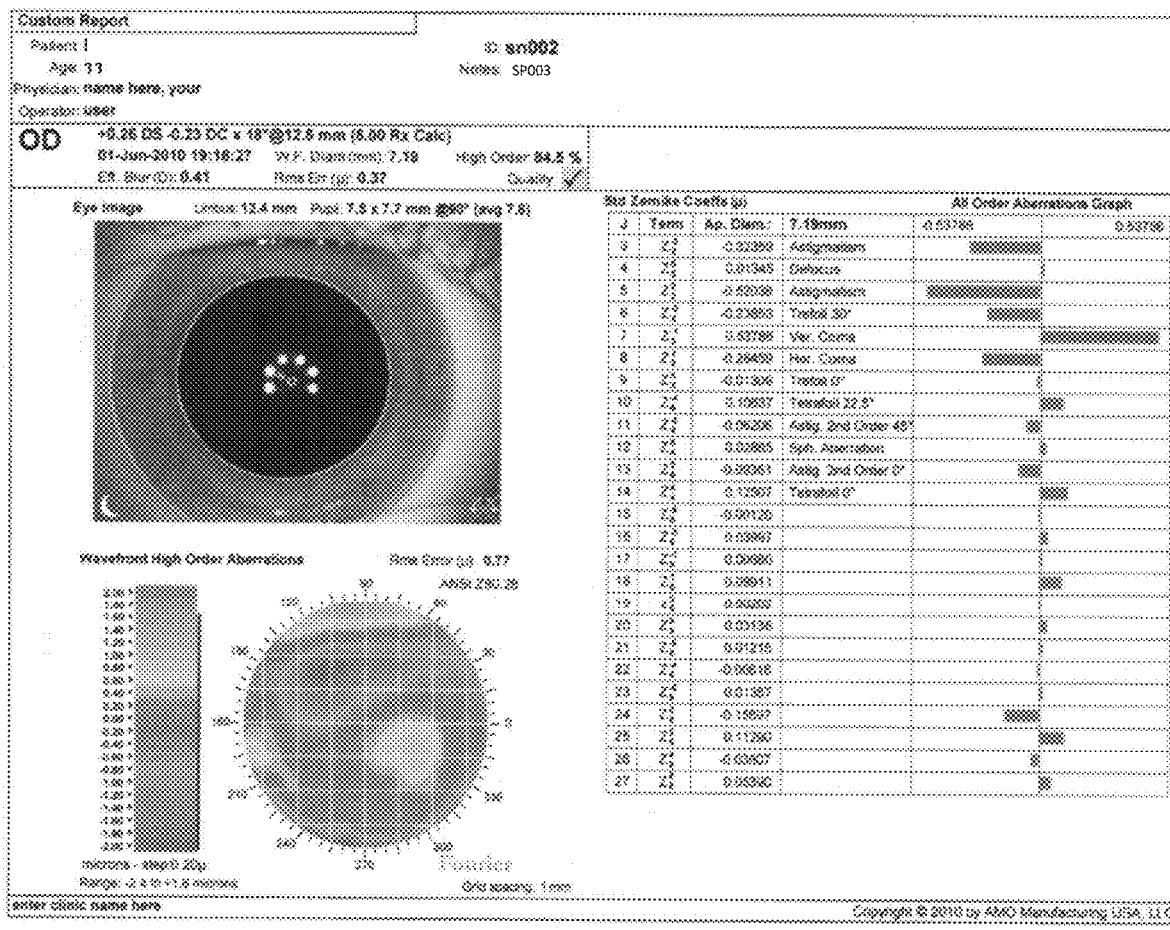
FIG. 15B shows a snapshot of a computer screen showing results of (1) a visual image of the patient's pupil, (2) a contour plot of wavefront measurements, and (3) a table listing the Zernike coefficients for the first twenty-seven Zernike polynomials, for a patient's bare eye fitted with a contact lens (+1.5D), according to the present invention.
Figure 16A:
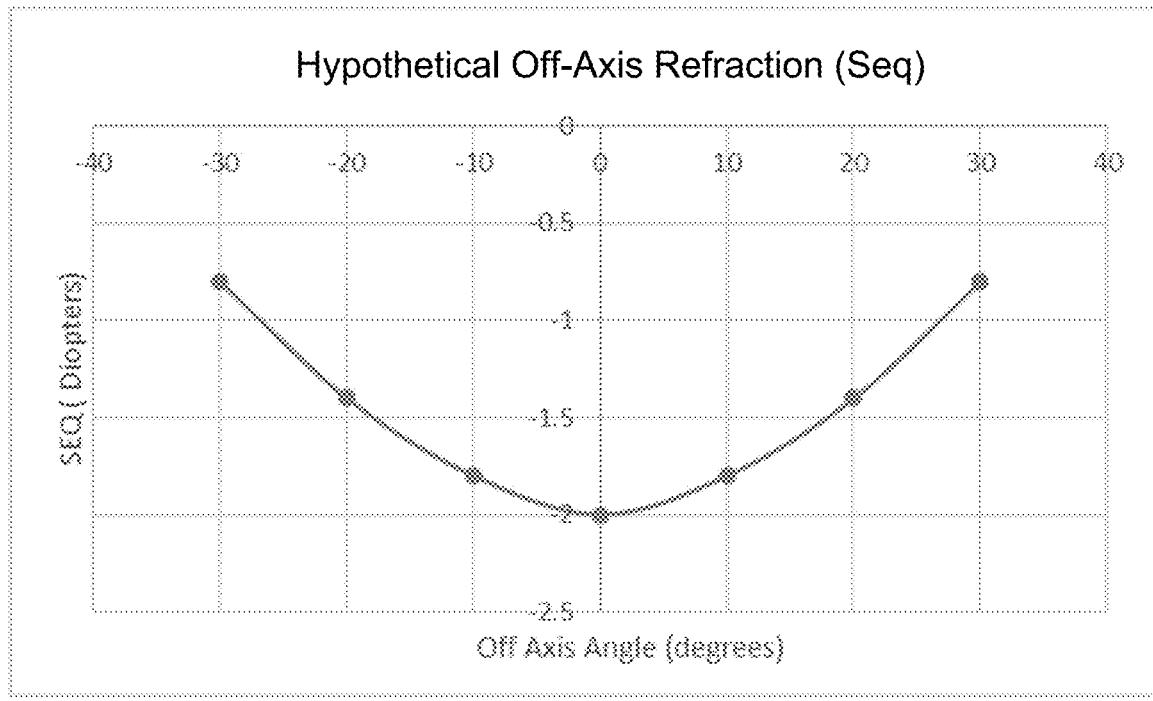
FIG. 16A shows a hypothetical off-axis refraction profile (Sphere, S) that this invention is intended to measure.
Figure 16B:
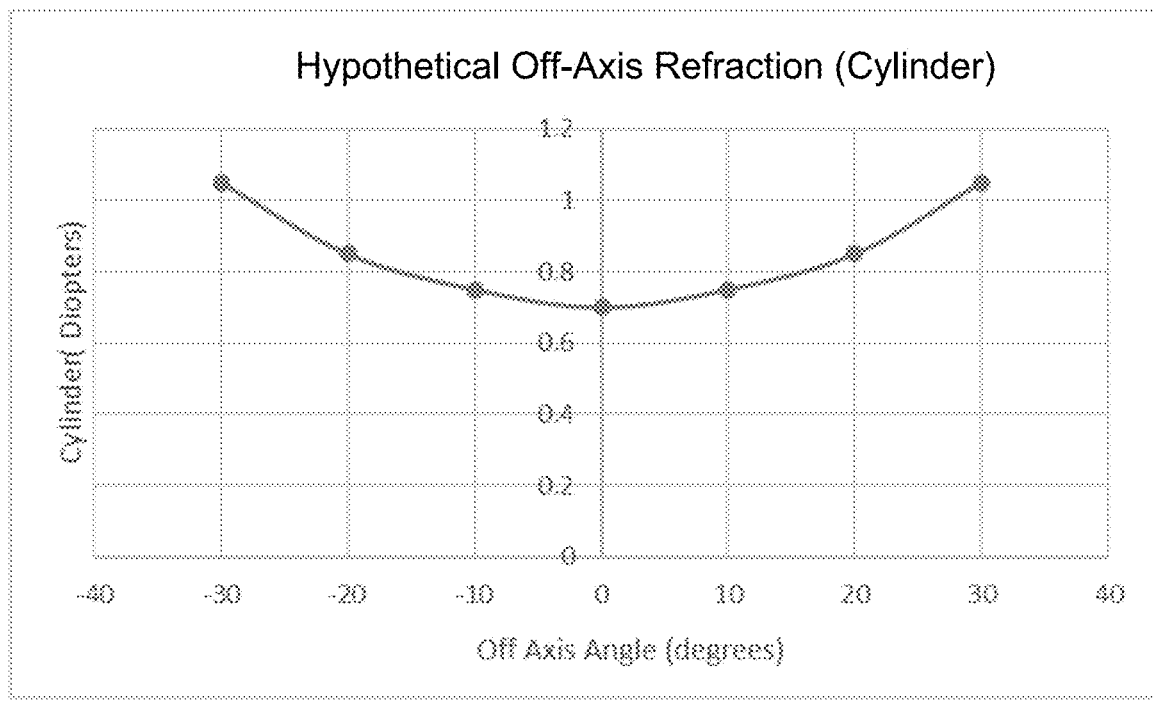
FIG. 16B is a hypothetical cylinder off-axis profile (Cylinder, C) that this invention is intended to measure.
Figure 17:
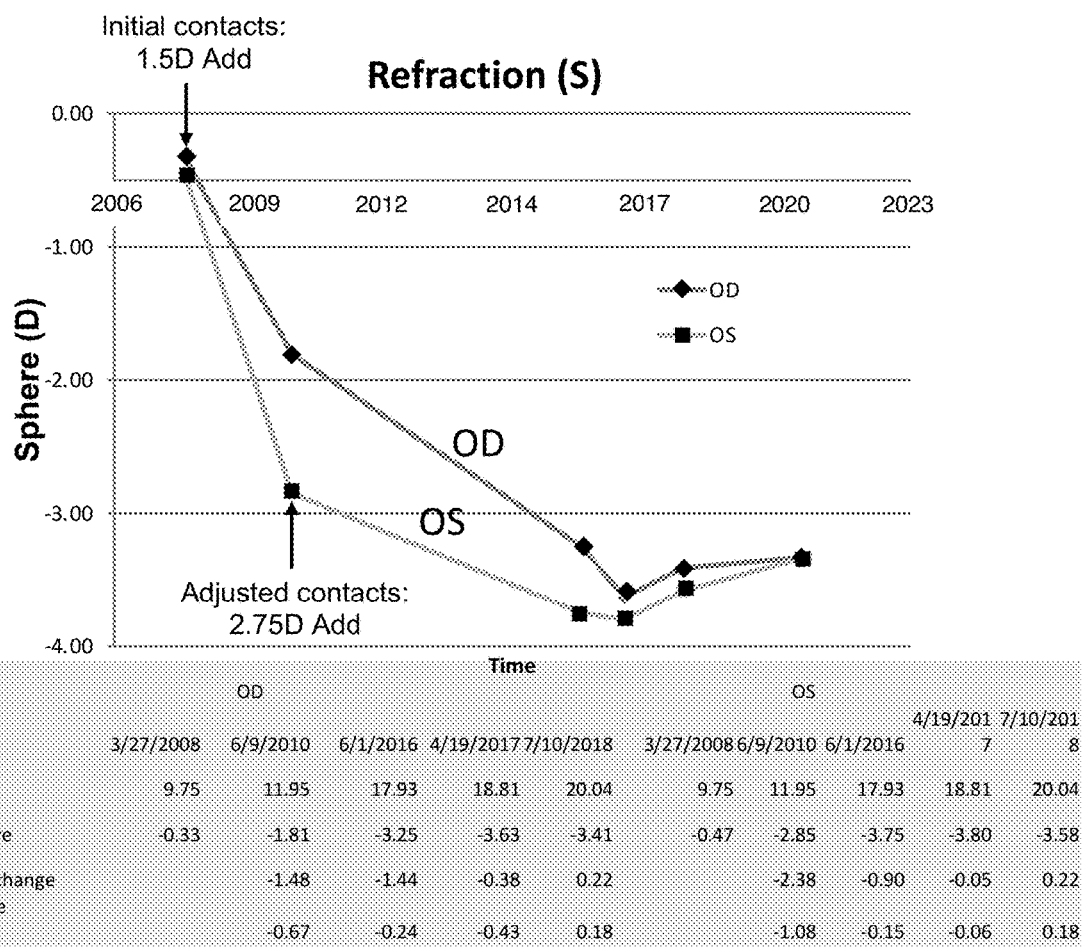
FIG. 17 shows a plot of a patient's refraction over a long period of time (13 years), illustrating the progression of myopia as the patient ages, according to the present invention.

FIG. 15B shows a snapshot of a computer screen showing: (1) a visual image of the patient's pupil, (2) a contour plot of wavefront measurements, and (3) a table listing the Zernike coefficients for the first twenty-seven Zernike polynomials, for a patient's bare eye fitted with a contact lens (+1.5D peripheral Add), according to the present invention. Initially, the lowest add value was used (+1.5D). Measuring through this contact lens, the results shown in FIG. 15B show that the spherical aberration is reduced to nearly zero. The RMS values for all the other Zernike coefficients are less than 0.54 microns, which is considerably improved over the initial trial contact lens shown in FIG. 15A. However, in order for Smith's Peripheral Defocus Theory to work, it is necessary to reverse the sign of the subject's spherical aberration FIG. 17 shows a plot of the progression of a patient's measured refraction over a long period of time (12 years), illustrating the development of myopia as the patient ages from 10 to 22 years old. The initial contact lenses were provided with +1.5D peripheral Add in 2008. Note the change in slope of the Sphere (D) vs time plot in 2010, which coincides with adjusting her contacts with a +2.75D peripheral Add. One eye is more myopic than the other eye, which is not un-common.

Figure 18:
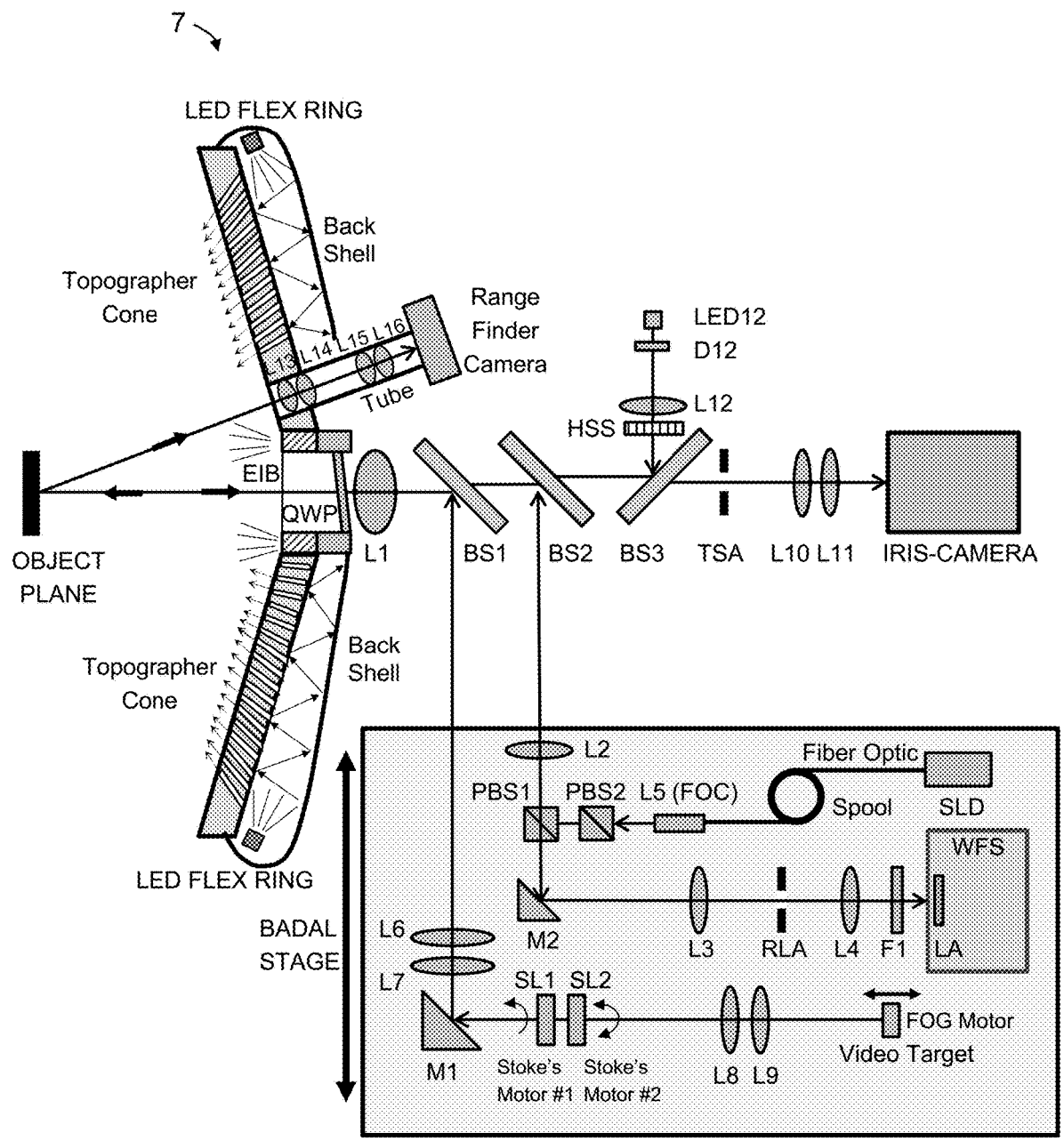
FIG. 18 shows a schematic optical layout of another embodiment of an aberrometer instrument, called NextWave™.

FIG. 18 shows a schematic optical layout of another embodiment of an aberrometer optical instrument, according to the present invention. This NextWave™ aberrometer comprises seven different optical paths:
1. Iris Camera path;
2. Topographer path;
3. Helmholtz path;
4. Probe Bean path;
5. Wavefront Sensor path;
6. Visual Target path; and
7. Range Finder Camera path.

In FIG. 18, the Iris Camera Path goes through QWP, L1, BS1, BS2, B3, TSA, L11, L12 and onto the Iris Camera. Light for the Iris Camera Path comes from the eye illumination board (EIB). The Topographer Path goes from a pattern of lighted holes in the Topographer Cone, with light reflecting off the cornea and passing through the Iris Camera Path. The Helmholtz path starts with light from LED12 going through diffuser D12, then Lens12, and then through the Helmholtz Source HHS (a plate with holes in it), reflects off BS3 through BS2, BS1, L1, QWP, reflects off the cornea, and then light reverses and goes back through QWP, L1, BS1, BS2, BS3, TSA, L10, L11 and on to the Iris Camera. The Probe Beam path starts at the super luminescent laser diode (SLD), goes through a fiber optic cable, coiled in a spool for mechanical convenience, through a Fiber Optic Collimator (FOC) (L5), goes through PBS2, reflects off PBS1, goes through L2, reflects off BS2, goes through BS1, L1, QWP and then through the cornea, forming a spot of light on the retina. Some of that light scatters off the retina, leaves the eye and goes back into the instrument along the Wavefront Sensor path (as described next).

In FIG. 18, the Wavefront Sensor path goes through QWP, L1, BS1 reflects off BS2, through L2, PBS1, reflects off M2, through L3, RLA, L4, F1 (Filter 1) and onto the wavefront sensor WFS. Light going into the Wavefront Sensor path comes from the Probe Beam (described above). The Visual Target Path goes through QWP, L1, reflects off BS1, goes through L6, L7, reflects off M1, goes through Stokes Lens1, Stokes Lens2, L8, L9 then reaches the video target (VT). The Range Finder Camera path goes through L13, L14, L15 and L16 and then onto the Range Finder Camera. The lenses are contained in a small tube that fits through the Topographer cone. The LED FLEX RING's purpose is to illuminate backside of the topographer cone. A backside baffle contains the light from LED FLEX RING. The topographer cone has a plurality of NC-machined holes (e.g., 800 holes) that all point towards a central point (i.e., the eye at the object plane), which collimates light originating from backside LED strip lights (similar to a Helmholtz light source (HHS) towards the object plane. The light sources can all be infrared wavelength, or a mixture of visible and infrared wavelengths.

Figure 19:
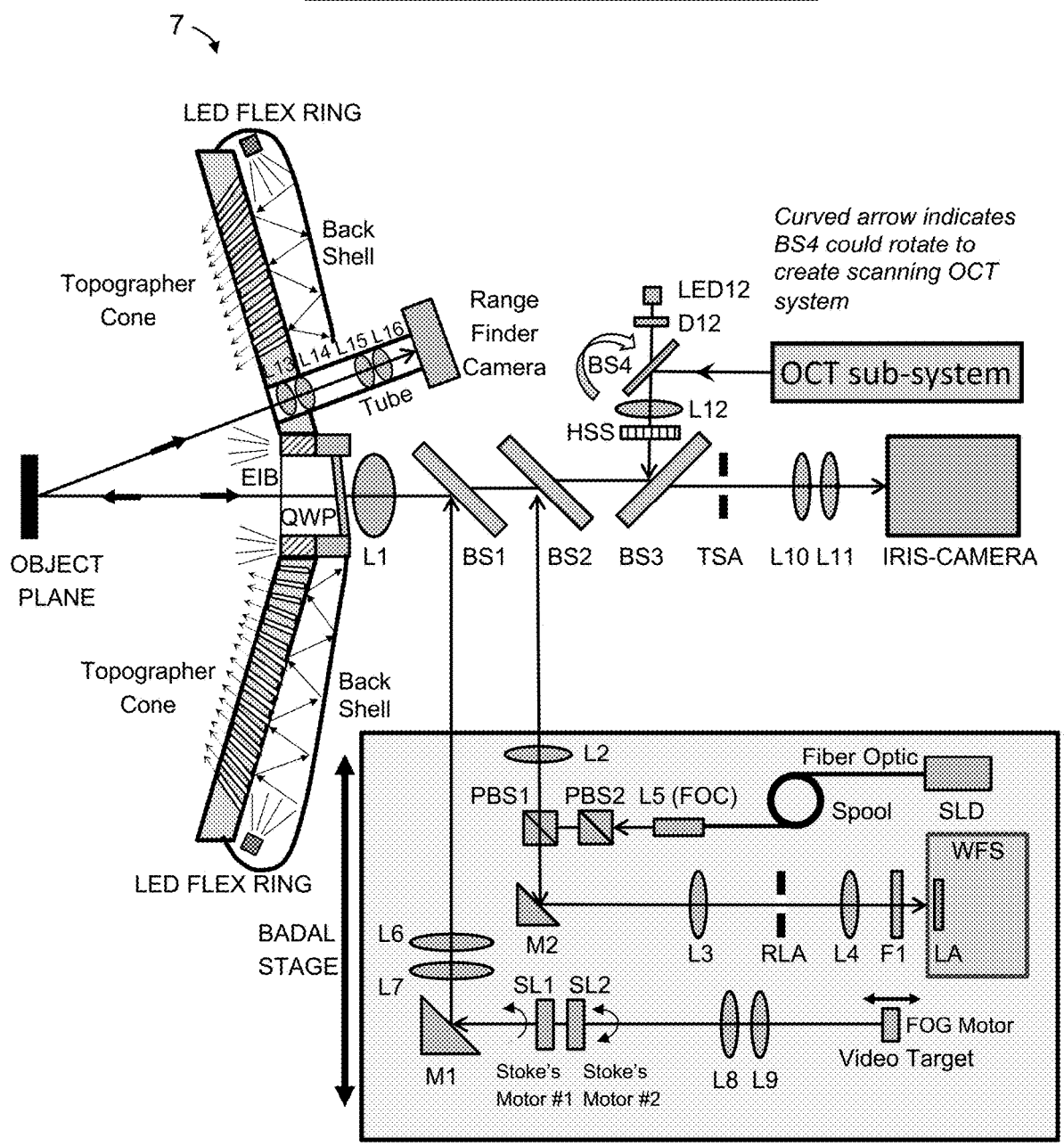
FIG. 19 shows a schematic optical layout of another embodiment of an aberrometer optical instrument, called NextWave™.

FIG. 19 shows a schematic optical layout of another embodiment of an aberrometer optical instrument, according to the present invention. An Optical Coherence Tomography (OCT) sub-system has been added to the main optical path. Light from the OCT sub-system is redirected off of beamsplitter BS4, which can have scanning capability, as indicated by the curved arrow in FIG. 19. Then, the light from BS4 goes through lens12 and through the Helmholtz source (HHS) onto beamsplitter BS3, which redirects the light onto the main optical path and towards the eye.

Figure 20:
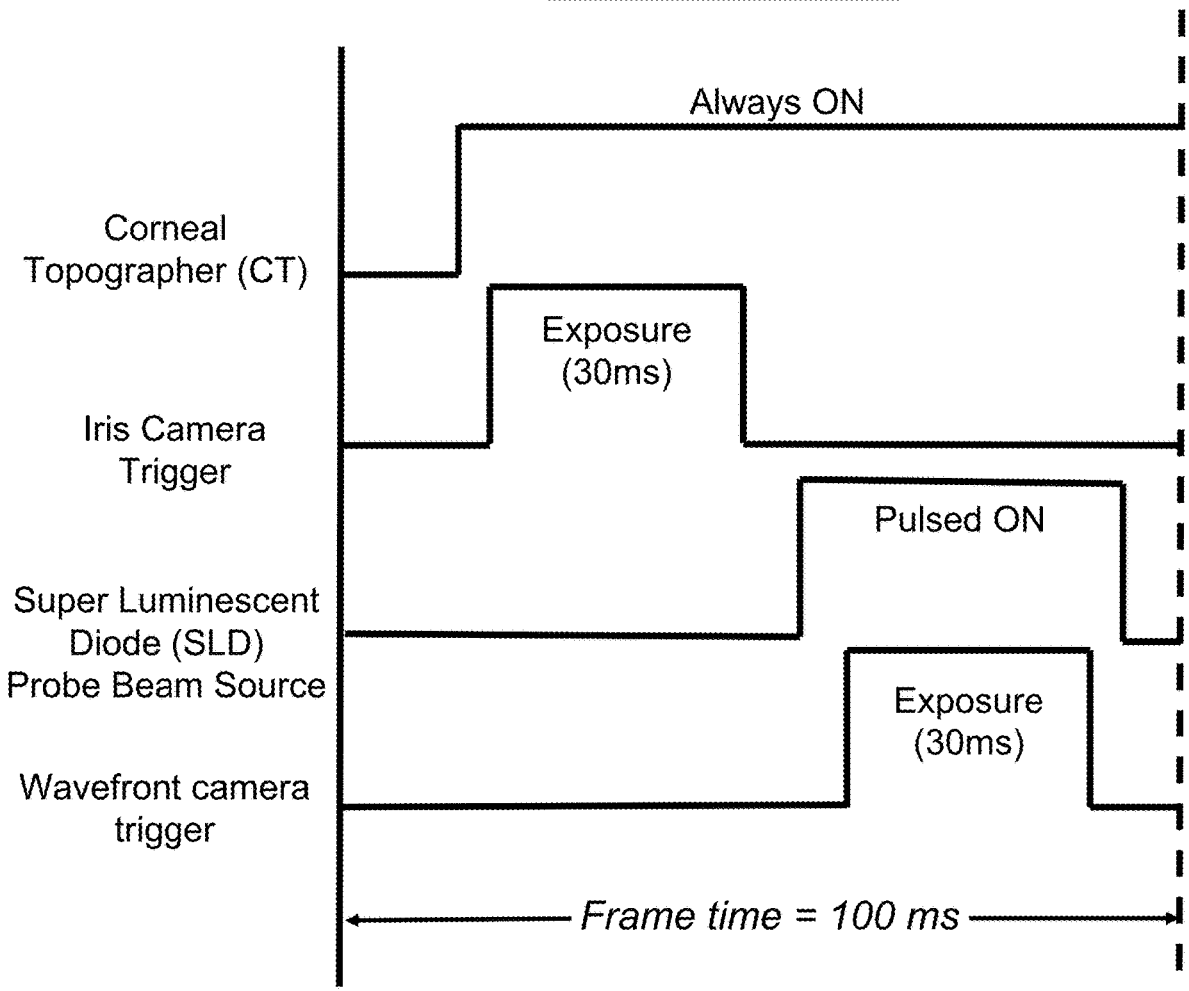
FIG. 20 shows a graph illustrating a first example of timing sequences of key system components of a generic optical instrument for a single frame time=100 ms.

FIG. 20 shows a graph illustrating a first example of timing sequences of key system components of a generic optical instrument for a single frame time=100 ms. The corneal topographer (CT) component is always ON (or, it may be pulsed as often as needed). Next, the iris visual camera triggers ON for an exposure period of, for example, 30 ms. Then, after the iris camera turns OFF, the Super Luminescent Diode (SLD) turns ON for approximately 40 ms. During the time the SLD is ON, the wavefront camera triggers ON for an exposure period of, for example, 30 ms. This entire process is repeated with a cycle frequency of about 10 Hz.

Figure 21:
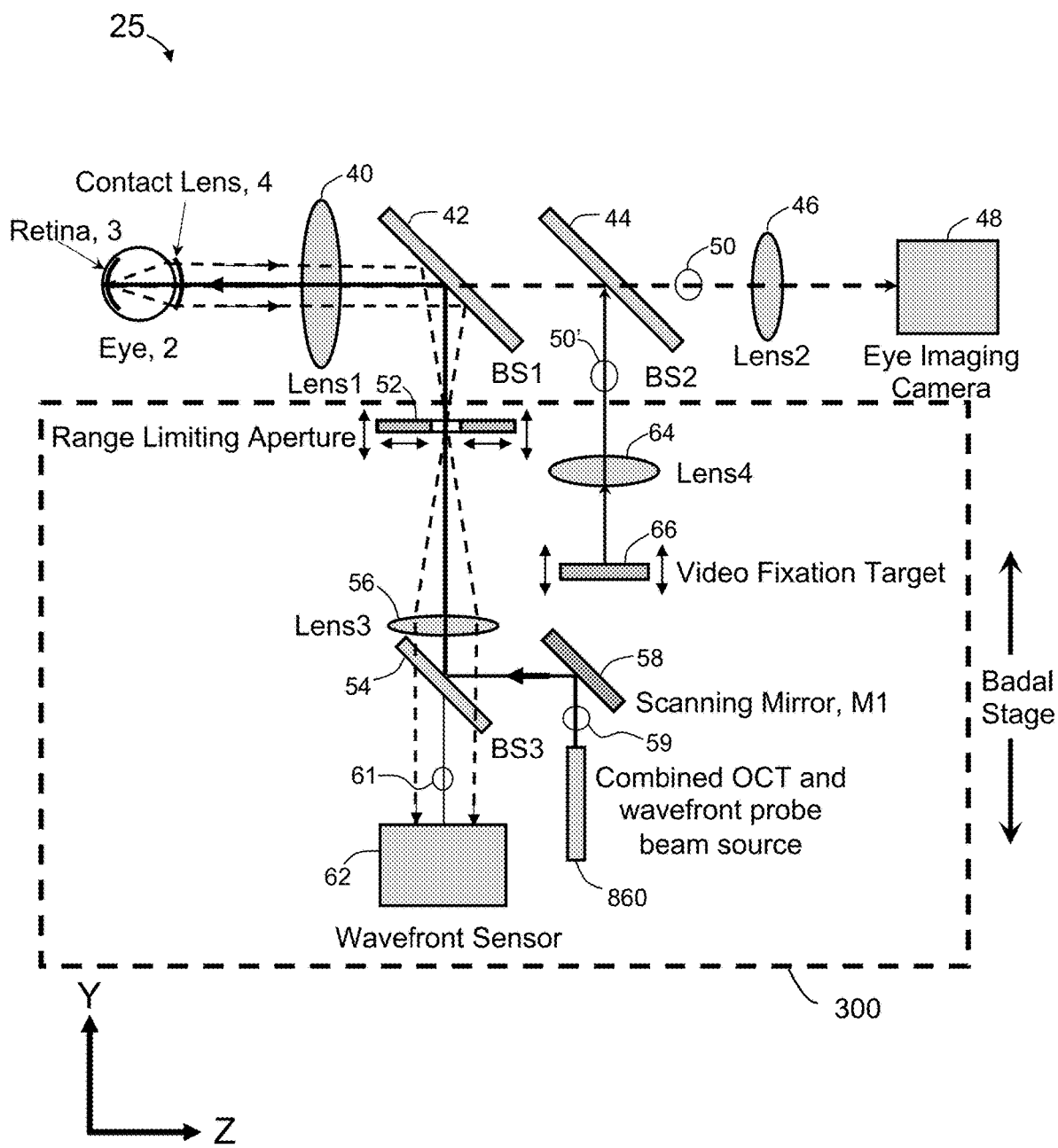
FIG. 21 shows a schematic optical configuration of a tenth embodiment of the present invention.

FIG. 21 is modified from FIG. 5 to represent a system that combines scanning OCT and off-axis refraction measurements. In FIG. 5, item 60 is labeled "probe beam source". To represent the addition of a scanning OCT system, item 860 is changed to read: "Combined OCT and Wavefront probe beam." Item 860 is a long rectangle because that matches the physical appearance of an optical fiber collimator. The light source for the wavefront and OCT both travel through the same optical fiber. In a practical system, it is advantageous to use commercially-available light sources of wavelengths that match transmission characteristics of the ocular media. One first variation uses a wavefront SLD source of 840 nm and an OCT SLD source of 1060 nm. A second variation uses a wavefront SLD source of 840 nm and OCT SLD source of 1310 nm. A third variation uses the same SLD for both wavefront and OCT, so the wavelengths would be same in both systems. The reasoning behind the different wavelengths is the following. The water in the eye blocks out wavelengths band around 1000 nm. But there is transmission band at 1060 to 1100 nm. So, there are a lot of commercially-available 1060 nm OCT systems for measuring the eye, especially systems that measure the retina. The wavelength of 1310 nm does not transmit well in the eye. But, there are a lot of low-cost optical parts available at 1310 nm because it is a communication band for internet and telephone fiber optics. So, people in optometry have made a lot of 1310 nm OCT systems. Mostly 1310 nm systems only measure the front of the eye because of poor transmission to the retina. But, Heidelberg Engineering, Inc. sells a 1310 nm OCT system that can measure back to the retina.

In all of the embodiments of the present invention, the optical instruments can rapidly multiplex (interleave) between wavefront sensing and visual iris imaging. This allows the clinician to create a dynamic sequence of measurements with both wavefront sensing (WFS) and iris imaging being interleaved, thereby allowing the clinician to find the position of the contact lens on the eye relative to the pupil, and to measure the eye's wavefront through the contact lens simultaneously (or near simultaneously, e.g., 30-40 ms apart), in real-time.

REFERENCES

[1] "Peripheral Refraction and Higher-Order Aberrations with Cycloplegia and Fogging Lenses using the BHVI-EyeMapper" Ravi Chandra Bakarajua, Cathleen Fedtkea, Klaus Ehrmannab, Darrin Falka, Varghese Thomasa, and Brien Anthony Holden, Journal of Optometry, Volume 9, January-March 2016, pages 5-12.
[2] Xin Wei, Larry Thibos "Design and validation of a scanning Shack Hartmann aberrometer for measurements over a wide field of view," Optics Express, 18 Jan. 2010, Vol. 18, No. 2, p 1134-1143
[3] Padmaja Sankaridurg, "Contact lenses to slow progression of myopia—Invited Revew," Clinical and Experimental Optometry, 2017, Vol. 100, pp 432-437

We claim:

1. A wide-field multi-axis aberrometer for simultaneously measuring on-axis and off-axis refractive properties and aberrations of an eye of a patient when looking into the aberrometer, the aberrometer comprising:
    (a) a main on-axis optical path, having a horizontal central axis;
    (b) an on-axis beamlet having an on-axis centerline that is coincident with the horizontal central axis of the main on-axis optical path;
        wherein the on-axis beamlet comprises the following free-space optical components:
            an on-axis probe beam source;
            a first on-axis beamsplitter;
            an on-axis front lens;
            an on-axis rear lens; and
            an on-axis wavefront sensor configured to receive light and measure on-axis refractions and on-axis higher-order aberrations of the eye;
        wherein the on-axis centerline of the on-axis beamlet is configured to point towards the eye at an angle of incidence equal to zero degrees;
    (c) an off-axis beamlet having an off-axis centerline configured to point towards the eye at an off-axis angle of incidence;
        wherein the off-axis beamlet comprises the following free-space optical components:
            an off-axis probe beam source;

an off-axis beamsplitter;
an off-axis front lens;
an off-axis rear lens; and
an off-axis wavefront sensor configured to receive light and measure off-axis refractions and off-axis higher-order aberrations of the eye;

wherein the off-axis beamsplitter is positioned to direct light travelling in the off-axis beamlet towards the eye at the off-axis angle of incidence;

wherein the off-axis angle of incidence of the off-axis beamlet ranges from 5 to 30 degrees, as measured angularly relative to the horizontal central axis of the main on-axis optical path;

wherein the on-axis beamlet further comprises a motorized Badal stage, comprising:
(a) an on-axis video fixation target;
(b) a second on-axis beamsplitter;
(c) the on-axis rear lens;
(d) the on-axis wavefront sensor; and
(e) a motorized stage configured to move components (a) through (d) as a unitary group; and wherein the aberrometer further comprises:
(1) a third on-axis beamsplitter located along the main on-axis optical path;
(2) a first on-axis mirror coincident with the main on-axis optical path;
(3) a third on-axis lens coincident with the main on-axis optical path; and
(4) an on-axis alignment camera coincident with the main on-axis optical path;

wherein the third on-axis beamsplitter is located between the on-axis front lens and the on-axis rear lens;

wherein the first on-axis mirror is located between the third on-axis beamsplitter and the third on-axis lens;

wherein the third on-axis lens is located between the first on-axis mirror and the on-axis alignment camera.

2. The wide-field multi-axis aberrometer of claim 1, further comprising four off-axis beamlets.

3. The wide-field multi-axis aberrometer of claim 1,
wherein the on-axis front lens and the on-axis rear lens of the on-axis beamlet are configured to form an on-axis telecentric teleobjective imaging system; and
wherein the off-axis front lens and the off-axis rear lens of the off-axis beamlet are configured to form an off-axis telecentric teleobjective imaging system.

4. The wide-field multi-axis aberrometer of claim 1, wherein the off-axis centerline of the off-axis beamlet is rotated at $\theta=15°$ relative to the on-axis centerline of the main on-axis optical path.

5. The wide-field multi-axis aberrometer of claim 1, wherein the on-axis front lens, the on-axis rear lens, the off-axis front lens, and the off-axis rear lens each comprise a plastic, singlet lens.

6. The wide-field multi-axis aberrometer of claim 1, further comprising a movable video fixation target configured to move along the main on-axis optical path.

7. The wide-field multi-axis aberrometer of claim 1, further comprising an Optical Coherence Tomography (OCT) subsystem that is coincident with the main on-axis optical path.

8. The wide-field multi-axis aberrometer of claim 1, wherein the on-axis probe beam source and the off-axis probe beam source each comprise a super-luminescent diode (SLD) emitting light at an infrared wavelength.

* * * * *